(12) United States Patent
Nakazato et al.

(10) Patent No.: US 6,852,732 B2
(45) Date of Patent: Feb. 8, 2005

(54) TETRAHYDROPYRIDINO OR PIPERIDINO HETEROCYLIC DERIVATIVES

(75) Inventors: Atsuro Nakazato, Tokyo (JP); Toshihito Kumagai, Tokyo (JP); Taketoshi Okubo, Tokyo (JP); Kazuya Kameo, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/311,277

(22) PCT Filed: Jul. 4, 2001

(86) PCT No.: PCT/JP01/05806

§ 371 (c)(1), (2), (4) Date: Aug. 25, 2003

(87) PCT Pub. No.: WO02/02549

PCT Pub. Date: Jan. 10, 2002

(65) Prior Publication Data

US 2004/0034061 A1 Feb. 19, 2004

(30) Foreign Application Priority Data

Jul. 5, 2000 (JP) ......................................... 2000-204021
Sep. 6, 2000 (JP) ......................................... 2000-270535

(51) Int. Cl.$^7$ ............................................. A01N 43/42
(52) U.S. Cl. ........................ 514/307; 546/144; 546/139; 544/235; 514/310; 514/248

(58) Field of Search ................................. 514/307, 310, 514/248; 546/144, 139; 544/235

(56) References Cited

U.S. PATENT DOCUMENTS 3,753,988 A * 8/1973 Rodway et al. ............. 544/237
6,187,781 B1    2/2001 Nakazato et al.

FOREIGN PATENT DOCUMENTS

| EP | 1 176 146 | 1/2002 |
| JP | 11-335373 | 12/1999 |
| JP | 11-335376 | 12/1999 |
| JP | 2000-86663 | 3/2000 |
| WO | WO 98/42699 | 10/1998 |
| WO | WO 98/47874 A1 | 10/1998 |
| WO | WO 99/01454 A1 | 1/1999 |
| WO | WO 00/53604 | 9/2000 |

OTHER PUBLICATIONS

European Search Report dated Aug. 23, 2004.

* cited by examiner

*Primary Examiner*—Charanjit S. Aulakh
(74) *Attorney, Agent, or Firm*—Sughrue Mion, PLLC

(57) ABSTRACT

A tetrahydropyridino or piperidino heterocyclic derivative represented by the formula [I]:

$$\text{A-Het} \qquad\qquad [\text{I}]$$

has a high affinity for CRF receptors and is effective against diseases in which CRF is considered to be involved.

4 Claims, No Drawings

TETRAHYDROPYRIDINO OR PIPERIDINO HETEROCYLIC DERIVATIVES

TECHNICAL FIELD

The present invention relates to a therapeutic agent for diseases in which corticotropin releasing factor (CRF) is considered to be involved, such as depression, anxiety, Alzheimer's disease, Parkinson's disease, Huntington's chorea, eating disorder, hypertension, gastral diseases, drug dependence, cerebral infarction, cerebral ischemia, cerebral edema, cephalic external wound, inflammation, immunity-related diseases, alpecia, etc.

BACKGROUND ART

CRF is a hormone comprising 41 amino acids (Science, 213, 1394–1397, 1981; and J. Neurosci., 7, 88–100, 1987), and it is suggested that CRF plays a core role in biological reactions against stresses (Cell. Mol. Neurobiol., 14, 579–588, 1994; Endocrinol., 132, 723–728, 1994; and Neuroendocrinol. 61, 445–452, 1995). For CRF, there are the following two paths: a path by which CRF acts on peripheral immune system or sympathetic nervous system through hypothalamus-pituitary-adrenal system, and a path by which CRF functions as a neurotransmitter in central nervous system (in Corticotropin Releasing Factor: Basic and Clinical Studies of a Neuropeptide, pp. 29–52, 1990). Intraventricular administration of CRF to hypophy-sectomized rats and normal rats causes an anxiety-like symptom in both types of rats (Pharmacol. Rev., 43, 425–473, 1991; and Brain Res. Rev., 15, 71–100, 1990). That is, there are suggested the participation of CRF in hypothalamus-pituitary-adrenal system and the pathway by which CRF functions as a neurotransmitter in central nervous system.

The review by Owens and Nemeroff in 1991 summarizes diseases in which CRF is involved (Pharmacol. Rev., 43, 425–474, 1991). That is, CRF is involved in depression, anxiety, Alzheimer's disease, Parkinson's disease, Huntington's chorea, eating disorder, hypertension, gastral diseases, drug dependence, inflammation, immunity-related diseases, etc. It has recently been reported that CRF is involved also in epilepsy, cerebral infarction, cerebral ischemia, cerebral edema, and cephalic external wound (Brain Res. 545, 339–342, 1991; Ann. Neurol. 31, 48–498, 1992; Dev. Brain Res. 91, 245–251, 1996; and Brain Res. 744, 166–170, 1997). Accordingly, antagonists against CRF receptors are useful as therapeutic agents for the diseases described above.

An object of the present invention is to provide an antagonist against CRF receptors which is effective as a therapeutic or prophylactic agent for diseases in which CRF is considered to be involved, such as depression, anxiety, Alzheimer's disease, Parkinson's disease, Huntington's chorea, eating disorder, hypertension, gastral diseases, drug dependence, epilepsy, cerebral infarction, cerebral ischemia, cerebral edema, cephalic external wound, inflammation, immunity-related diseases, alpecia, etc.

DISCLOSURE OF THE INVENTION

The present inventors earnestly investigated tetrahydropyridino or piperidino heterocyclic derivatives and consequently found novel tetrahydropyridino or piperidino heterocyclic derivatives having a high affinity for CRF receptors, whereby the present invention has been accomplished.

The present invention is explained below.

The present invention is a tetrahydropyridino or piperidino heterocyclic derivative represented by the following formula [I]:

$$A\text{-Het} \quad\quad [I]$$

wherein A is a group represented by the following formula [II] or [III]:

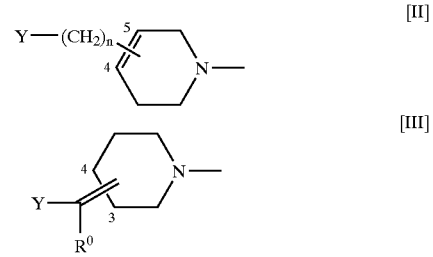

wherein the position of substitution by the $Y\text{—}(CH_2)_n\text{—}$ group of the group represented by the formula [II] is 4-position or 5-position, the position of substitution by the $Y\text{—}C(R^0)=$ group of the group represented by the formula [III] is 3-position or 4-position, $R^0$ is a hydrogen atom, a $C_{1-5}$alkyl group, a $C_{3-8}$cycloalkyl group or a $C_{3-8}$cycloalkyl-$C_{1-5}$alkyl group, n is an integer of 0 to 5, and Y is a cyano group, a group represented by the formula $\text{—}CONR^1(R^2)$ (wherein each of $R^1$ and $R^2$, which may be the same or different, is a hydrogen atom, a $C_{1-5}$alkyl group, a $C_{3-8}$cycloalkyl group, a $C_{3-8}$cycloalkyl-$C_{1-5}$alkyl group, a $C_{1-5}$alkoxy-$C_{1-5}$alkyl group, a $C_{3-8}$cycloalkyloxy-$C_{1-5}$alkyl group or a phenyl group, or $R^1$ and $R^2$, when taken together with the adjacent nitrogen atom, represent a 5- to 8-membered saturated heterocyclic group represented by the formula:

(wherein B is $CH_2$, NH, N—$C_{1-5}$alkyl, N—$C_{3-8}$cycloalkyl, N—$C_{1-5}$alkyl-$C_{3-8}$cycloalkyl, O or S)) or a group represented by the formula $\text{—}CO_2R^3$ (wherein $R^3$ is a hydrogen atom, a $C_{1-5}$alkyl group, a $C_{3-8}$cycloalkyl group, a $C_{3-8}$cycloalkyl-$C_{1-5}$alkyl group, a $C_{1-5}$alkoxy-$C_{1-5}$alkyl group, a $C_{3-8}$cycloalkyloxy-$C_{1-5}$alkyl group or a phenyl group), and Het is any of heterocyclic groups represented by the following formulas form(01) to form(20):

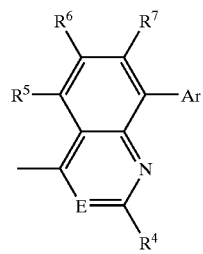

form (01)

-continued
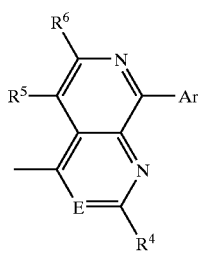
form (02)
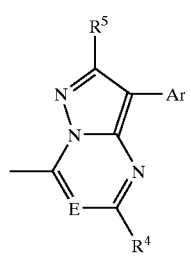
form (03)
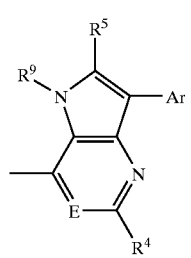
form (04)
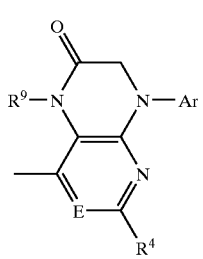
form (05)
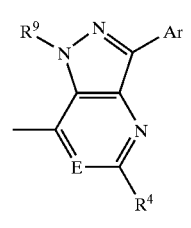
form (06)
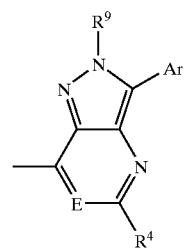
form (07)
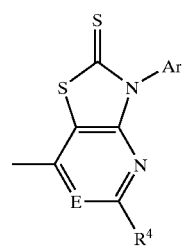
form (08)
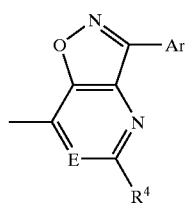
form (09)
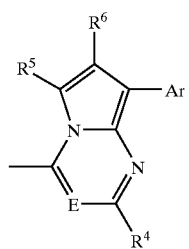
form (10)
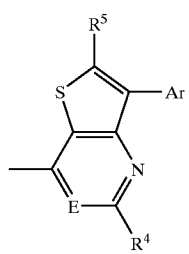
form (11)
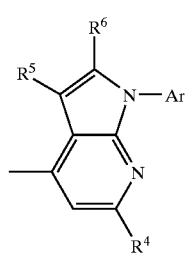
form (12)
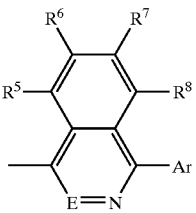
form (13)

form (14)

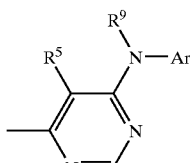

form (15)

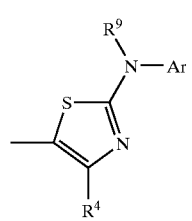

form (16)

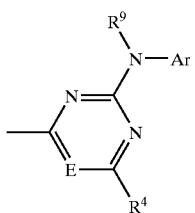

form (17)

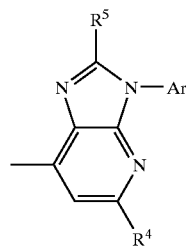

form (18)

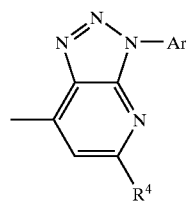

form (19)

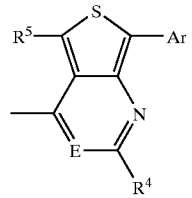

form (20)

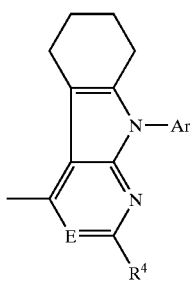

wherein E is CH or N, $R^4$ is a hydrogen atom, a $C_{1-5}$alkyl group, a $C_{3-8}$cycloalkyl group, a $C_{3-8}$cycloalkyl-$C_{1-5}$alkyl group, a hydroxyl group, a $C_{1-5}$alkoxy group, a $C_{3-8}$cycloalkyloxy group, or a group represented by the formula —N($R^{10}$)$R^{11}$ (wherein each of $R^{10}$ and $R^{11}$, which may be the same or different, is a hydrogen atom, a $C_{1-5}$alkyl group, a $C_{3-8}$cycloalkyl group or a $C_{3-8}$cycloalkyl-$C_{1-5}$alkyl group), each of $R^5$, $R^6$, $R^7$ and $R^8$, which may be the same or different, is a hydrogen atom, a halogen atom, a $C_{1-5}$alkyl group, a $C_{3-8}$cycloalkyl group, a $C_{3-8}$cycloalkyl-$C_{1-5}$alkyl group, a hydroxyl group, a $C_{1-5}$alkoxy group, a $C_{3-8}$cycloalkyloxy group, a group represented by the formula —N($R^{12}$)$R^{13}$ (wherein each of $R^{12}$ and $R^{13}$, which may be the same or different, is a hydrogen atom, a $C_{1-5}$alkyl group, a $C_{3-8}$cycloalkyl group or a $C_{3-8}$cycloalkyl-$C_{1-5}$alkyl group), a group represented by the formula —CO$_2$$R^{14}$ (wherein $R^{14}$ is a hydrogen atom, a $C_{1-5}$alkyl group, a $C_{3-8}$cycloalkyl group, a $C_{3-8}$cycloalkyl-$C_{1-5}$alkyl group, a $C_{1-5}$alkoxy-$C_{1-5}$alkyl group, a $C_{3-8}$cycloalkyloxy-$C_{1-5}$alkyl group or a phenyl group), a cyano group, a nitro group, a $C_{1-5}$alkylthio group, a trifluoromethyl group or a trifluoromethoxy group, $R^9$ is a hydrogen atom, a $C_{1-5}$alkyl group, a $C_{2-5}$alkenyl group, a $C_{2-5}$alkynyl group, a $C_{3-8}$cycloalkyl group or a $C_{3-8}$cycloalkyl-$C_{1-5}$alkyl group, and Ar is an aryl or heteroaryl group unsubstituted or substituted with 1 to 3 substituents which may be the same or different and are selected from halogen atoms, $C_{1-5}$alkyl groups, $C_{1-5}$alkoxy groups, $C_{1-5}$alkylthio groups, trifluoromethyl group, trifluoromethoxy group and groups represented by the formula —N($R^{15}$)$R^{16}$ (wherein each of $R^{15}$ and $R^{16}$, which may be the same or different, is a hydrogen atom or a $C_{1-5}$alkyl group);

or a pharmaceutically acceptable salt thereof or its hydrate.

The terms used in the present specification have the following meanings.

The term "$C_{1-5}$alkyl group" means a straight chain or branched chain alkyl group of 1 to 5 carbon atoms, such as methyl, ethyl, propyl, isopropyl, butyl, isobutyl, t-butyl, pentyl, isopentyl or the like. The term "$C_{2-5}$alkenyl group" means a straight chain or branched chain alkenyl group of 2 to 5 carbon atoms, such as vinyl, 1-propenyl, 2-propenyl, 1-methylvinyl or the like. The term "$C_{2-5}$alkynyl group" means a straight chain or branched chain alkynyl group of 2 to 5 carbon atoms, such as ethynyl, 2-propynyl or the like. The term "$C_{3-8}$cycloalkyl group" means a cyclic alkyl group of 3 to 8 carbon atoms, such as cyclopropyl, cyclobutyl, cyclopentyl, cyclohexyl, cycloheptyl or the like. The term "$C_{3-8}$cycloalkyl-$C_{1-5}$alkyl group" means a substituted $C_{1-5}$alkyl group having the above-mentioned $C_{3-8}$cycloalkyl group as the substituent, such as cyclopropylmethyl, cyclopropylethyl, cyclopentylethyl or the like.

For B, the term "N—$C_{1-5}$alkyl" means a group having a $C_{1-5}$alkyl group as a substituent on the nitrogen atom. The term "N—$C_{3-8}$cycloalkyl" means a group having a $C_{3-8}$cycloalkyl group as a substituent on the nitrogen atom. The term "N—$C_{1-5}$alkyl-$C_{3-8}$cycloalkyl" means a group having a $C_{3-8}$cycloalkyl-$C_{1-5}$alkyl group as a substituent on the nitrogen atom.

The term "halogen atom" means a fluorine atom, a chlorine atom, a bromine atom or an iodine atom. The term "$C_{1-5}$alkoxy group" means a straight chain or branched chain alkoxy group of 1 to 5 carbon atoms, such as methoxy, ethoxy, propoxy, isopropyloxy, butoxy, isobutyloxy, pentyloxy, isopentyloxy or the like. The term "$C_{3-8}$cycloalkyloxy group" means a cyclic alkoxy group of 3 to 8 carbon atoms, such as cyclopropyloxy, cyclobutyloxy, cyclopentyloxy or the like. The term "$C_{3-8}$alkoxy-$C_{1-5}$alkyl group" means a substituted $C_{1-5}$alkyl group having a $C_{1-5}$alkoxy group as the substituent, such as methoxymethyl, 2-ethoxyethyl or the like. The term "$C_{3-8}$cycloalkyloxy-$C_{1-5}$alkyl group" means a substituted $C_{1-5}$alkyl group having a $C_{3-8}$cycloalkoxy group as the substituent, such as cyclopropyloxymethyl, 2-cyclo-propyloxyethyl or the like. The term "$C_{1-5}$alkylthio group" means a straight chain or branched chain alkylthio group of 1 to 5 carbon atoms, such as methylthio, ethylthio, propylthio or the like.

The term "aryl group" means a phenyl group, a naphthyl group or the like. The term "heteroaryl group" means a heterocyclic group having in its ring 1 to 4 atoms which may be the same or different and are selected from nitrogen, oxygen and sulfur, such as pyridyl, quinolyl, indolyl, benzofuranyl, benzothiadiazolyl, benzofurazanyl, quinoxalinyl or the like. Therefore, the substituted aryl or heteroaryl group includes, for example, 2,4,6-trimethylphenyl group, 2,4,6-tribromophenyl group, 2,4-dibromo-6-chlorophenyl group, 2,4-dichlorophenyl group, 2,4,6-trichlorophenyl group, 2-methyl-4-methoxyphenyl group, 2,4-dibromo-6-fluorophenyl group, 2,4-dibromo-6-methylphenyl group, 2,4-dibromo-6-methoxyphenyl group, 2,4-dibromo-6-methylthiophenyl group, 2,6-dibromo-4-isopropylphenyl group, 2,6-dibromo-4-trifluoromethylphenyl group, 2-chloro-4-trifluoromethylphenyl group, 2-chloro-4-trifluoromethoxyphenyl group, 6-dimethylamino-4-methylpyridin-3-yl group, 2-chloro-6-trifluoromethylpyridin-3-yl group, 2-chloro-6-trifluoromethoxypyridin-3-yl group, 2-chloro-6-methoxypyridin-3-yl group, 2-trifluoromethyl-6-methoxypyridin-3-yl group, 2-chloro-6-difluoromethylpyridin-3-yl group, 2-methyl-6-methoxypyridin-3-yl group, 2,6-dimethoxypyridin-3-yl group, 5,7-dimethyl-2,1,3-benzothiadiazol-4-yl group, 5,7-dimethylbenzofurazan-4-yl group, 6,8-dimethyl-quinoxalin-5-yl group, 5,7-dichloro-2,1,3-benzothiadiazol-4-yl, 5,7-dichlorobenzofurazan-4-yl group and 6,8-dichloroquinoxalin-5-yl group.

The pharmaceutically acceptable salt in the present invention includes, for example, salts with an inorganic acid such as sulfuric acid, hydrochloric acid, phosphoric acid or the like; salts with an organic acid such as acetic acid, oxalic acid, lactic acid, tartaric acid, fumaric acid, maleic acid, citric acid, benzenesulfonic acid, methanesulfonic acid, p-toluenesulfonic acid or the like; and salts with a metal ion such as lithium ion, sodium ion, potassium ion, calcium ion, magnesium ion, zinc ion or the like.

Preferable examples of the compound of the present invention are as follows.

That is, preferable are compounds of the formula [I] in which A is a group represented by the formula [II]. More preferable are compounds of the formula [I] in which A is a group represented by the formula [II], Y is a carbamoyl group and n is 0 or 1. In addition, preferable are compounds of the formula [I] in which Het is a heterocyclic group represented by form(01) or form(12). More preferable are compounds of the formula [I] in which Het is a heterocyclic group represented by form(01) or form(12), and Ar is a phenyl group having two or three substituents which may be the same or different and are selected from halogen atoms, $C_{1-5}$alkyl groups, $C_{1-5}$alkoxy groups, $C_{1-5}$alkylthio groups, trifluoromethyl group and trifluoromethoxy group. Still more preferable are compounds of the formula [I] in which Het is a heterocyclic group represented by form(01) or form(12), and Ar is a phenyl group having two or three substituents which may be the same or different and are selected from chlorine atom, trifluoromethyl group and trifluoromethoxy group.

The compound of the formula [I] can be produced, for example, by any of the processes shown in the following reaction schemes 1 to 7 (in the following reaction schemes, A, Het, $R^1$, $R^2$, $R^3$, $R^4$, $R^5$, $R^6$ and $R^7$ are as defined above, $R^{17}$ is a $C_{1-5}$alkyl group or a phenyl group, and $X^4$ is a chlorine atom, a bromine atom, an iodine atom, a methanesulfonyloxy group, a benzenesulfonyloxy group, a toluenesulfonyloxy group or a trifluoromethanesulfonyloxy group).

Reaction Scheme 1.

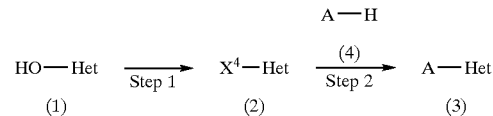

Step 1:

Compound (2) can be obtained by halogenation or sulfonylation of the hydroxyl group of Compound (1). Here, the halogenation refers to reaction with a halogenating reagent such as phosphorus oxychloride, phosphorus pentachloride, sulfuryl chloride, thionyl chloride, thionyl bromide, oxalyl chloride or the like in the presence or absence of, for example, N,N-dimethylaniline or N,N-diethylaniline without a solvent or in an inert solvent such as a hydrocarbon (e.g., benzene and toluene) or a halogen-containing solvent (e.g., chloroform and dichloromethane). The sulfonylation refers to reaction with a sulfonylating reagent such as methanesulfonyl chloride, p-toluenesulfonyl chloride, trifluoromethanesulfonic acid anhydride, N-phenylbis (trifluoromethanesulfonimide) or the like in the presence or absence of a base in an inert solvent such as an ether (e.g., diethyl ether, tetrahydrofuran, 1,4-dioxane and 1,2-dimethoxyethane), a hydrocarbon (e.g., benzene and toluene), an amide (e.g., N,N-dimethylformamide and N-methylpyrrolidone), acetonitrile, dimethyl sulfoxide, pyridine, or a mixture of solvents selected from these inert solvents. Here, the base includes, for example, organic bases such as triethylamine, diisopropylethylamine, pyridine, 1,8-diazabicyclo[5.4.0]-7-undecene and the like; and inorganic bases such as sodium hydride, potassium hydride, sodium carbonate, potassium carbonate, sodium hydrogencarbonate, sodium amide and the like.

Step 2:

Compound (3), the compound of the present invention, can be obtained by reacting Compound (2) with Compound (4) in an inert solvent in the presence or absence of a base. Here, the base includes, for example, amines such as triethylamine, diisopropyl-ethylamine, pyridine and the like; inorganic bases such as sodium carbonate, potassium carbonate, sodium hydrogencarbonate, potassium hydrogencarbonate, sodium hydroxide, barium hydroxide, sodium hydride and the like; metal alcoholates such as sodium methoxide, sodium ethoxide, potassium tert-butoxide and the like; metal amides such as sodium amide, lithium diisopropylamide and the like; and Grignard reagents such as methylmagnesium bromide and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene and the like; amides such as N,N-dimethylformamide, N-methyl-pyrrolidone and the like; acetonitrile; dimethyl sulfoxide; pyridine; water; and mixtures of solvents selected from these inert solvents.

Compound (9) of the present invention can be synthesized according also to the following reaction scheme 2.

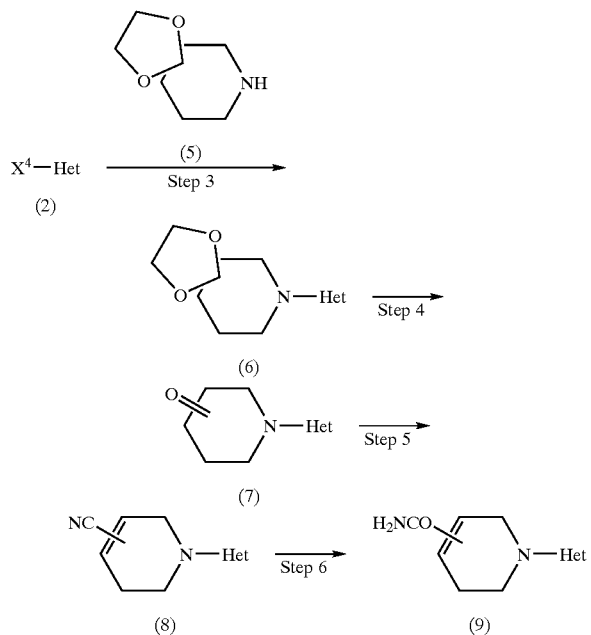

Step 3:

Compound (6) can be obtained by reacting Compound (2) with Compound (5) in an inert solvent in the presence or absence of a base. Here, the base includes, for example, amines such as triethylamine, diisopropylethylamine, pyridine and the like; inorganic bases such as sodium carbonate, potassium carbonate, sodium hydrogencarbonate, potassium hydrogencarbonate, sodium hydroxide, barium hydroxide, sodium hydride and the like; metal alcoholates such as sodium methoxide, sodium ethoxide, potassium tert-butoxide and the like; metal amides such as sodium amide, lithium diisopropylamide and the like; and Grignard reagents such as methylmagnesium bromide and the like. The inert solvent includes, for example, alcohols such as methanol, ethanol, isopropyl alcohol, ethylene glycol and the like; ethers such as diethyl ether, tetrahydrofuran, 1,4-dioxane, 1,2-dimethoxyethane and the like; hydrocarbons such as benzene, toluene and the like; amides such as N,N-dimethylformamide, N-methyl-pyrrolidone and the like; acetonitrile; dimethyl sulfoxide; pyridine; water; and mixtures of solvents selected from these inert solvents.

Step 4:

Compound (6) can be converted to Compound (7) by removing the acetal protective group of Compound (6) by conventional hydrolysis under acidic conditions (see Theodora W. Greene and Peter G. W. Wuts "Protective Groups in Organic Synthesis").

Step 5:

Compound (7) can be converted to Compound (8) by reacting Compound (7) in the presence of a cyanating agent such as sodium cyanide, potassium cyanide, trimethylsilyl cyanide or the like in an inert solvent such as an alcohol (e.g., methanol, ethanol, isopropyl alcohol and ethylene glycol), an ether (e.g., diethyl ether, tetrahydrofuran, 1,4-dioxane and 1,2-dimethoxyethane), acetonitrile, acetic acid, water, or a mixture of solvents selected from these inert solvents; and then reacting the cyanation product with, for example, phosphorus oxychloride, thionyl chloride, methanesulfonyl chloride, p-toluenesulfonyl chloride or trifluoroacetic anhydride in the presence or absence of an organic base such as pyridine, triethylamine or diisopropylethylamine in an inert solvent such as a halogen-containing solvent (e.g., dichloromethane and chloroform), an ether (e.g., diethyl ether, tetrahydrofuran, 1,4-dioxane and 1,2-dimethoxyethane), a hydrocarbon (e.g., benzene and toluene) or the like.

Step 6:

Compound (8) can be converted to Compound (9) of the present invention by reacting the cyano group of Compound (8) by using, for example, sulfuric acid, hydrogen chloride and formic acid singly or in combination of two or more thereof, in an inert solvent such as a halogen-containing solvent (e.g., dichloromethane and chloroform), an ether (e.g., diethyl ether, tetrahydrofuran, 1,4-dioxane and 1,2-dimethoxyethane), a hydrocarbon (e.g., benzene and toluene), water or a mixture of solvents selected from these inert solvents.

In addition, Compound (10) and Compound (17) of the present invention can be obtained according also to the following reaction scheme 3.

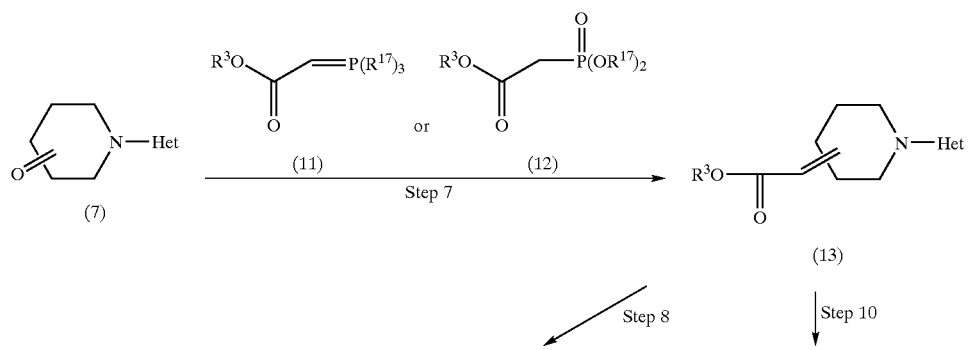

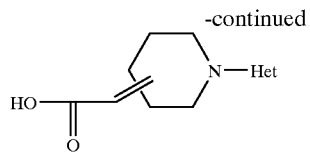

(14)

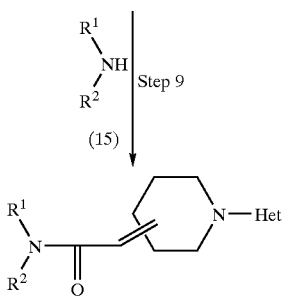

(10)

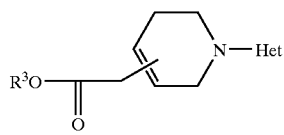

(16)

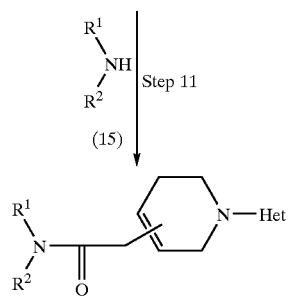

(17)

Step 7:

Compound (7) can be converted to Compound (13) by reacting Compound (7) with either Compound (11) or Compound (12) in an inert solvent in the presence or absence of a base. Here, the base includes, for example, sodium hydride, potassium hydride, sodium methoxide, potassium tert-butoxide, n-butyllithium, lithium bis(trimethylsilyl) amide, sodium amide and potassium carbonate. If necessary, 18-crown-6 ether, 15-crown-5 ether, tetramethylethylenediamine, hexamethylphosphoramide and the like can be used as an additive. The inert solvent includes, for example, ethers such as diethyl ether, tetrahydrofuran, 1,2-dimethoxyethane and the like; hydrocarbons such as benzene, toluene and the like; alcohols such as ethanol, methanol and the like; amides such as N,N-dimethylformamide, N-methylpyrrolidone and the like; tetramethylurea; dimethyl sulfoxide; water; and mixtures of solvents selected from these inert solvents.

Step 8:

When $R^3$ of Compound (13) is a group other than a hydrogen atom, Compound (13) can be converted to Compound (14) of the present invention by conventional hydrolysis of the ester portion under acidic or basic conditions (see Theodora W. Greene and Peter G. W. Wuts "Protective Groups in Organic Synthesis").

Step 9:

Compound (10) of the present invention can be obtained by amidation of Compound (14). Here, the amidation refers to general amidation of the carboxyl group, and refers to any of the following reactions: the reaction of Compound (15) with a mixed acid anhydride obtained by the reaction of Compound (14) with a haloformic acid ester (e.g., ethyl chloroformate and isobutyl chloroformate) or an acid halide (e.g., benzoyl chloride and pivaloyl chloride) in the presence of a base such as N-methylmorpholine, triethylamine or the like; the reaction of Compound (14) with Compound (15) in the presence of a condensing agent such as N,N'-dicyclohexylcarbodiimide (DCC), 1-(3-dimethylaminopropyl)-3-ethylcarbodiimide (EDC), carbonyldiimidazole (CDI), diphenylphosphorylazide (DPPA), diethyl cyanophosphate or the like and optionally an additive such as 1-hydroxybenzotriazole (HOBt), N-hydroxysuccinimide, 4-dimethylaminopyridine or the like; and the reaction of Compound (15) with an acid halide obtained by the reaction of Compound (14) with a halogenating reagent such as thionyl chloride, oxalyl chloride, carbon tetrabromide-triphenylphosphine or the like.

Step 10:

Compound (13) can be converted to Compound (16) by reacting Compound (13) in the presence of an acid or a base in an inert solvent. Here, the acid includes, for example, inorganic acids such as hydrogen chloride, hydrobromic acid, sulfuric acid and the like; and organic acids such as acetic acid, trifluoroacetic acid, p-toluenesulfonic acid and the like. The base includes inorganic bases such as sodium hydroxide, potassium hydroxide, potassium carbonate and the like. The inert solvent includes, for example, ethers such as diethyl ether, tetrahydrofuran, 1,2-dimethoxyethane and the like; hydrocarbons such as benzene, toluene and the like; alcohols such as ethanol, methanol and the like; amides such as N,N-dimethylformamide, N-methyl-pyrrolidone and the like; tetramethylurea; dimethyl sulfoxide; water; acetone; and mixtures of solvents selected from these inert solvents. When $R^3$ is a group other than a hydrogen atom, employment of a solvent for reaction composed of water alone or a mixture of water and one or more other solvents makes it possible to carry out the conversion of $R^3$ to a hydrogen atom and the conversion of Compound (13) to Compound (16) simultaneously.

Step 11:

When $R^3$ is a group other than a hydrogen atom, $R^3$ is converted to a hydrogen atom by the same procedure as in Step 8, after which Compound (17) of the present invention can be obtained by the same reaction as in Step 9.

Compounds (22), (23) and (24) can be synthesized according also to the following reaction scheme 4.

Reaction Scheme 4

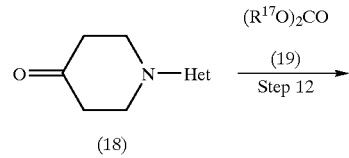

(18)

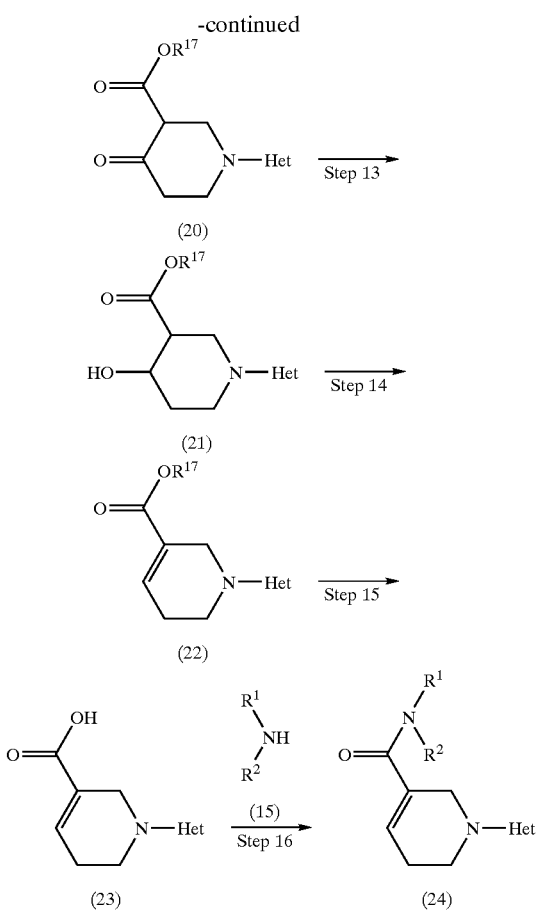

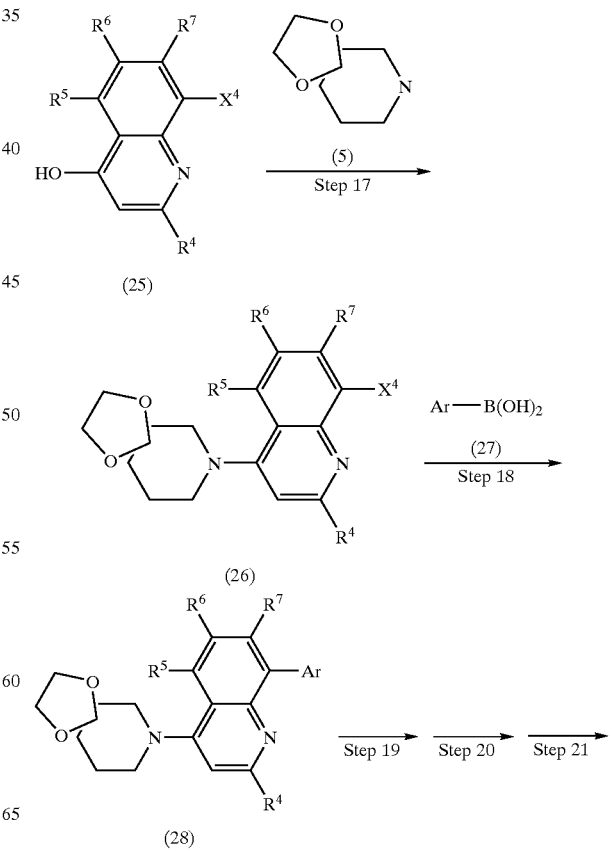

4-dimethylamino-pyridine, triethylamine, diisopropylethylamine, 1,8-diazabicyclo[5.4.0]-7-undecene or the like in an inert solvent such as a halogen-containing solvent (e.g., dichloromethane and chloroform), an ether (e.g., diethyl ether, tetrahydrofuran, 1,4-dioxane and 1,2-dimethoxyethane), a hydrocarbon (e.g., benzene and toluene) or the like, or by reacting Compound (21) with, for example, sulfuric acid, trifluoroacetic acid or formic acid in an inert solvent such as a halogen-containing solvent (e.g., dichloromethane and chloro-form), an ether (e.g., diethyl ether, tetrahydrofuran, 1,4-dioxane and 1,2-dimethoxyethane), a hydrocarbon (e.g., benzene and toluene) or the like.

Step 15:

Compound (22) can be converted to Compound (23) of the present invention by converting the ester portion of Compound (22) to a carboxyl group by the same procedure as in Step 8.

Step 16:

Compound (23) can be converted to Compound (24) of the present invention by reacting Compound (23) with Compound (15) by the same procedure as in Step 9.

Compound (29) of the present invention can be synthesized according also to the following reaction scheme 5.

Step 12:
Compound (20) can be obtained by reacting Compound (18) with Compound (19) in an inert solvent in the presence of a base. Here, the inert solvent includes, for example, ethers such as diethyl ether, tetrahydrofuran, 1,2-dimethoxyethane and the like; hydrocarbons such as benzene, toluene and the like; alcohols such as ethanol, methanol and the like; amides such as N,N-dimethylformamide, N-methylpyrrolidone and the like; tetramethylurea; dimethyl sulfoxide; and mixtures of solvents selected from these inert solvents. The base includes, for example, amines such as triethylamine, diisopropylethylamine, pyridine and the like; inorganic bases such as sodium hydride, potassium hydride, sodium carbonate and the like; metal alcoholates such as sodium methoxide, sodium ethoxide, potassium tert-butoxide and the like; alkyl metals such as n-butyllithium, tert-butyllithium, phenyllithium and the like; and metal amides such as lithium diisopropyl-amide, lithium bis(trimethylsilyl)amide, sodium amide and the like.

Step 13:
Compound (20) can be converted to Compound (21) by reduction of the ketone portion represented by hydride reduction using sodium boron hydride, and hydrogenation (see Ahmed F. Abdel-Magid "Reductions in Organic Synthesis").

Step 14:
Compound (21) can be converted to Compound (22) by reacting Compound (21) with, for example, phosphorus oxychloride, thionyl chloride, methane-sulfonyl chloride, p-toluenesulfonyl chloride or trifluoroacetic anhydride in the presence or absence of an organic base such as pyridine,

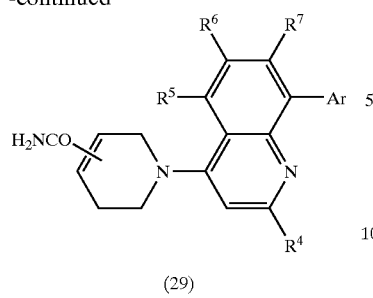

(29)

Step 17:

Compound (26) can be obtained by halogenating or sulfonylating the hydroxyl group of Compound (25) by the same procedure as in Step 1, and then reacting the halogenation or sulfonylation product with Compound (5) in an inert solvent in the presence or absence of a base. Here, the base includes, for example, organic bases such as triethylamine, diisopropylethylamine, pyridine, 1,8-diazabicyclo[5.4.0]-7-undecene and the like; and inorganic bases such as sodium hydride, potassium hydride, sodium carbonate, potassium carbonate, sodium hydrogencarbonate, sodium amide and the like. The inert solvent includes, for example, ethers such as diethyl ether, tetrahydrofuran, 1,4-dioxane, 1,2-dimethoxyethane and the like; hydrocarbons such as benzene, toluene and the like; amides such as N,N-dimethylformamide, N-methylpyrrolidone and the like; acetonitrile; dimethyl sulfoxide; pyridine; and mixtures of solvents selected from these inert solvents.

Step 18:

Compound (26) can be converted to Compound (28) by reacting Compound (26) with an aryl-boric acid derivative (27) in an inert solvent in the presence of a base, a zerovalence palladium complex (e.g., tetrakis(triphenylphosphine)palladium and tetrakis-(tributylphosphine)palladium) or a divalent palladium complex (e.g., palladium acetate and palladium chloride) and optionally a phosphine (e.g., triphenyl-phosphine and tributylphosphine). Here, the base includes, for example, inorganic bases such as sodium carbonate, sodium hydrogencarbonate, potassium carbonate, barium hydroxide, sodium hydroxide and the like; and organic bases such as triethylamine, diisopropylethylamine, pyridine, 4-dimethylamino-pyridine and the like. The inert solvent includes, for example, halogen-containing solvents such as dichloro-methane, chloroform and the like; ethers such as diethyl ether, tetrahydrofuran, 1,4-dioxane, 1,2-dimethoxyethane and the like; hydrocarbons such as benzene, toluene and the like; alcohols such as methanol, ethanol and the like; water; and mixtures of solvents selected from these inert solvents.

Step 19, Step 20 and Step 21:

Compound (29) of the present invention can be obtained by carrying out Step 19, Step 20 and Step 21 in the same manner as for Step 4, Step 5 and Step 6, respectively.

Compound (32) of the present invention can be synthesized according also to the following reaction scheme 6.

Reaction Scheme 6

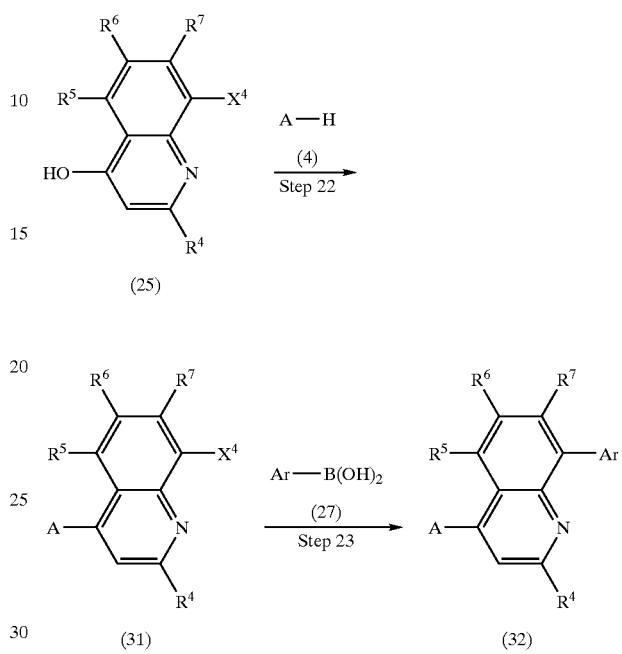

Compound (31) can be obtained by halogenating or sulfonylating the hydroxyl group of Compound (25) by the same procedure as in Step 1, and then reacting the halogenation or sulfonylation product with Compound (4) in an inert solvent in the presence or absence of a base. Here, the base includes, for example, organic bases such as triethylamine, diisopropylethylamine, pyridine, 1,8-diazabicyclo[5.4.0]-7-undecene and the like; and inorganic bases such as sodium hydride, potassium hydride, sodium carbonate, potassium carbonate, sodium hydrogencarbonate, sodium amide and the like. The inert solvent includes, for example, ethers such as diethyl ether, tetrahydrofuran, 1,4-dioxane, 1,2-dimethoxyethane and the like; hydrocarbons such as benzene, toluene and the like; amides such as N,N-dimethylformamide, N-methylpyrrolidone and the like; acetonitrile; dimethyl sulfoxide; pyridine; and mixtures of solvents selected from these inert solvents.

Step 23:

Compound (32) of the present invention can be obtained by the same procedure as in Step 18.

Compounds (33), (34) and (35) of the present invention can be synthesized according also to the following reaction scheme 7.

Reaction Scheme 7

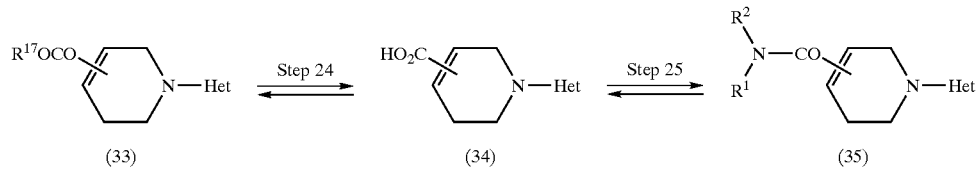

Step 24:
Compounds (33) and (34) of the present invention can be converted to each other by conventional protection and deprotection of the ester portion and the carboxylic acid portion (see Theodora W. Greene and Peter G. W. Wuts "Protective Groups in Organic Synthesis").

Step 25:
Compound (34) of the present invention can be converted to Compound (35) of the present invention by conventional amidation in the same manner as in Step 9. Compound (35) can be converted to Compound (34) by converting the amide portion of Compound (35) to a carboxylic acid by conventional hydrolysis (see Theodora W. Greene and Peter G. W. Wuts "Protective Groups in Organic Synthesis").

The compound of the present invention is useful as a therapeutic or prophylactic agent for diseases in which CRF is considered to be involved. For this purpose, the compound of the present invention can be formulated into tablets, pills, capsules, granules, powders, solutions, emulsions, suspensions, injections and the like by a conventional preparation technique by adding conventional fillers, binders, disintegrators, pH-adjusting agents, solvents, etc.

The compound of the present invention can be administered to an adult patient in a dose of 0.1 to 500 mg per day in one portion or several portions orally or parenterally. The dose can be properly increased or decreased depending on the kind of a disease and the age, body weight and symptom of a patient.

BEST MODE FOR CARRYING OUT THE INVENTION

The present invention is concretely explained with reference to the following examples and test example, but is not limited thereto.

EXAMPLE 1

Synthesis of 8-(2,4-dichlorophenyl)-4-(4-carbamoyl-1,2,3,6-tetrahydropyridin-1-yl)-2-methyl-quinoline (Compound 1-01)

After 60% sodium hydride (an oil dispersion) (79 mg) was washed with hexane and then suspended in N,N-dimethylformamide (3 mL), the suspension was cooled with ice. To the cooled suspension was added 8-(2,4-dichlorophenyl)-2-methyl-4-hydroxyquinoline (500 mg) all at once, and the resulting mixture was stirred under ice-cooling for 10 minutes and then at room temperature for another 30 minutes. To the solution thus obtained was added N-phenylbis(trifluoromethane-sulfonimide) (703 mg) all at once, and the resulting mixture was stirred at room temperature for 30 minutes.

To the resultant reaction mixture were added sodium hydrogencarbonate (413 mg) and 4-carbamoyl-1,2,3,6-tetrahydropyridine hydrochloride (533 mg), and the resulting mixture was vigorously stirred at 120° C. for 1 hour.

The reaction mixture thus obtained was cooled to room temperature and then separated with chloroform and water. The aqueous layer was extracted with chloroform and the combined organic layer was dried over anhydrous sodium sulfate, after which the desiccating agent was filtered off and the filtrate was concentrated under reduced pressure. The residue was purified by a silica gel column chromatography (silica gel: Wako Gel (C200), eluent: chloroform-methanol= 10:1), and the crystals thus obtained were washed with methanol and then tetrahydrofuran to obtain the title compound (156 mg).

m.p. 263.5–265.5° C.

Table 1, Table 2, Table 7, Table 17 and Table 18 list the compound obtained in Example 1 and compounds obtained by the same procedure as in Example 1.

EXAMPLE 2

Synthesis of 8-(2,4-dichlorophenyl)-4-(5-carbamoyl-1,2,3,6-tetrahydropyridin-1-yl)-2-methyl-quinoline (Compound 1-15)

(1) In phosphorus oxychloride (5 mL), 8-(2,4-dichlorophenyl)-2-methyl-4-hydroxyquinoline (2.0 g) was heated under reflux for 1 hour. The reaction mixture was cooled to room temperature and carefully poured into ice water, and the resulting mixture was separated with a saturated aqueous sodium hydrogen-carbonate solution and ethyl acetate. The organic layer was dried over anhydrous sodium sulfate, after which the desiccating agent was filtered off and the filtrate was concentrated under reduced pressure to obtain a solid (2.1 g).

(2) A mixture of the solid (200 mg) obtained in (1), 5-carbamoyl-1,2,3,6-tetrahydropyridine hydro-chloride (121 mg), diisopropylethylamine (240 mg) and ethanol (1 mL)-water (0.075 mL) was allowed to react in a sealed tube at 80° C. for 10 days. The reaction mixture was cooled to room temperature, poured into a saturated aqueous sodium hydrogencarbonate solution, and then extracted three times with chloroform. The combined organic layer was dried over anhydrous sodium sulfate, after which the desiccating agent was filtered off and the filtrate was concentrated under reduced pressure. The residue was purified by a silica gel column chromatography (silica gel: Wako Gel (C200), eluent: chloroform-methanol=10:1) and then crystallized from ethyl acetate to obtain the title compound (159 mg).

m.p. 230.0–232.0° C.

Table 1, Table 2, Tables 3 to 11, Table 13, Table 16, Table 19 and Table 20 list the compound obtained in Example 2 and compounds obtained by the same procedure as in Example 2.

EXAMPLE 3

Synthesis of 8-(2,4-dichlorophenyl)-4-(4-carbamoyl-1,2,3,6-tetrahydropyridin-1-yl)-2-methyl-quinoline (Compound 1-01)

(1) In N,N-dimethylformamide (50 mL), 4-chloro-8-(2,4-dichlorophenyl)-2-methylquinoline (3.3 g) obtained by the same procedure as in Example 2, (1) and 4-piperidone ethylene ketal (7.5 g) were stirred at 120° C. for 2 hours and then at 150° C. for 2 hours, and the resulting mixture was heated under reflux for 3.5 hours. The solvent was distilled off under reduced pressure, after which water and a saturated aqueous sodium hydrogencarbonate solution were added to the residue and the solid precipitated was collected by filtration. The obtained solid was purified by a silica gel column chromatography (silica gel: Wako Gel (C200), eluent: chloroform-methanol=10:1) to obtain 8-(2,4-dichlorophenyl)-4-(1,4-dioxa-8-azaspiro[4.5]dec-8-yl)-2-methylquinoline (3.2 g).

m.p. 179.5–181.5° C.

(2) In a mixture of 1 M hydrochloric acid (30 mL) and tetrahydrofuran (15 ml), 8-(2,4-dichlorophenyl)-4-(1,4-dioxa-8-azaspiro[4.5]dec-8-yl)-2-methylquinoline (3.2 g) was stirred at room temperature for 2 hours and then at 70° C. for 5.5 hours. The tetrahydrofuran was distilled off under reduced pressure, and the residue was made basic with a 41% aqueous sodium hydroxide solution under ice-cooling and extracted three times with ethyl acetate. The combined organic layer was dried over anhydrous sodium sulfate, after which the desiccating agent was filtered off and the filtrate was concentrated under reduced pressure.

The resultant residue was dissolved in ethanol (12.5 ml)-chloroform (6 mL), and potassium cyanide (5.4 g) was added thereto. To the mixture thus obtained was added acetic acid (4.4 mL) under ice-cooling over a period of 10 minutes, and the resulting mixture was stirred at room temperature for 6 hours. The reaction mixture was separated with ethyl acetate and a saturated aqueous sodium hydrogencarbonate solution and the organic layer was dried over anhydrous sodium sulfate, after which the desiccating agent was filtered off and the filtrate was concentrated under reduced pressure.

The resultant residue was dissolved in pyridine (15 mL), and phosphorus oxychloride (7.5 mL) was added thereto under ice-cooling. The reaction mixture was stirred at room temperature for 24 hours and then carefully poured into ice water. The reaction mixture thus treated was extracted three times with a mixed solvent of chloroform and methanol, and the combined organic layer was dried over anhydrous sodium sulfate, after which the desiccating agent was filtered off and the filtrate was concentrated under reduced pressure. The residue was purified by a silica gel column chromatography (silica gel: Wako Gel (C200), eluent: hexane-ethyl acetate=5:1) and then crystallized from diisopropyl ether to obtain 8-(2,4-dichlorophenyl)-2-methyl-4-(4-cyano-1,2,3,6-tetrahydro-pyridin-1-yl)quinoline (1.0 g).

m.p. 177.5–179.5° C.

(3) In 96% formic acid (5 mL) was dissolved 8-(2,4-dichlorophenyl)-2-methyl-4-(4-cyano-1,2,3,6-tetrahydropyridin-1-yl)quinoline (1.0 g), and hydrogen chloride gas was bubbled into the solution under ice-cooling to saturate the solution therewith. The reaction mixture was stirred at room temperature for 4 hours and then distilled under reduced pressure to remove the solvent. The residue was separated with chloroform and a saturated aqueous sodium hydrogen-carbonate solution, and the organic layer was dried over anhydrous sodium sulfate. The desiccating agent was filtered off and the filtrate was concentrated under reduced pressure. The residue was purified by a silica gel column chromatography (silica gel: Wako Gel (C200), eluent: chloroform-methanol=10:1) and then recrystallized from tetrahydrofuran to obtain the title compound (174 mg).

m.p. 263.5–265.5° C.

Table 1 and Table 14 list the compound obtained in Example 3 and a compound obtained by the same procedure as in Example 3.

EXAMPLE 4

Synthesis of 4-(4-carbamoyl-1,2,3,6-tetrahydropyridin-1-yl)-1-(2,4-dichlorophenyl)-2,3,6-trimethyl-1H-pyrrolo[2,3-b]pyridine (Compound 12-01)

(1) After 60% sodium hydride (an oil dispersion) (0.97 g) was washed with hexane and then suspended in N,N-dimethylformamide (10 mL), a solution of 1-(2,4-dichlorophenyl)-4-hydroxy-2,3,6-trimethyl-1H-pyrrolo[2,3-b]pyridine (6.50 g) in N,N-dimethyl-formamide (90 mL) was added dropwise thereto. The resulting mixture was stirred at 40° C. for 30 minutes, after which N-phenylbis(trifluoromethanesulfonimide) (8.65 g) was added thereto all at once, followed by stirring at room temperature for 30 minutes. To the solution thus obtained was added 4-piperidone ethylene ketal (16.4 g), and the reaction was carried out at 90° C. for 2 hours, at 100° C. for 1.5 hours, and then at 120° C. for 2.5 hours. After the reaction mixture was cooled to room temperature, a saturated aqueous ammonium chloride solution was poured thereinto, followed by extraction with ethyl acetate, and the organic layer was dried over anhydrous sodium sulfate. The desiccating agent was filtered off, after which the filtrate was concentrated under reduced pressure, and the residue was purified by a silica gel column chromato-graphy (silica gel: wako Gel (C200), eluent: hexane-ethyl acetate=3:1) to obtain 1-(2,4-dichlorophenyl)-4-(1,4-dioxa-8-azaspiro[4.5]dec-8-yl)-2,3,6-trimethyl-1H-pyrrolo[2,3-b]pyridine (5.23 g).

(2) After 1-(2,4-dichlorophenyl)-4-(1,4-dioxa-8-azaspiro[4.5]dec-8-yl)-2,3,6-trimethyl-1H-pyrrolo[2,3-b]-pyridine (5.21 g) was stirred in a mixture of 4 M hydrochloric acid (60 mL) and tetrahydrofuran (60 mL) at room temperature for 2.5 hours, 6 M hydrochloric acid (30 mL) was added thereto and the resulting mixture was stirred overnight. After completion of the reaction, the reaction mixture was poured into a saturated aqueous sodium hydrogen-carbonate solution and extracted three times with ethyl acetate. The combined organic layer was dried over anhydrous sodium sulfate, after which the desiccating agent was filtered off and the filtrate was concentrated under reduced pressure. The crystals thus obtained were washed with ethyl acetate to obtain 1-(2,4-dichlorophenyl)-4-(4-oxopiperidin-1-yl)-2,3,6-trimethyl-1H-pyrrolo[2,3-b]pyridine (3.83 g).

(3) In ethanol (10 mL)-chloroform (4 mL) was dissolved 1-(2,4-dichlorophenyl)-4-(4-oxopiperidin-1-yl)-2,3,6-trimethyl-1H-pyrrolo[2,3-b]pyridine (0.55 g), and potassium cyanide (0.91 g) was added thereto. To the resulting mixture was added acetic acid (0.75 mL) under ice-cooling over a period of 15 minutes, followed by stirring at room temperature for 2 hours. The reaction mixture was separated with ethyl acetate and a saturated aqueous sodium hydrogencarbonate solution and the organic layer was dried over anhydrous sodium sulfate, after which the desiccating agent was filtered off and the filtrate was concentrated under reduced pressure.

The resultant residue was dissolved in pyridine (6.4 mL), and phosphorus oxychloride (1.3 mL) was added thereto under ice-cooling. The reaction mixture was stirred at room temperature for 1 hour and then at 60° C. for 1 hour. The reaction mixture was carefully poured into ice water and extracted three times with ethyl acetate, and the combined organic layer was dried over anhydrous sodium sulfate, after which the desiccating agent was filtered off and the filtrate was concentrated under reduced pressure. The residue was purified by a silica gel column chromatography (silica gel: Wako Gel (C200), eluent: hexane-ethyl acetate=4:1) to obtain 4-(4-cyano-1,2,3,6-tetrahydropyridin-1-yl)-1-(2,4-dichlorophenyl)-2,3,6-trimethyl-1H-pyrrolo[2,3-b]pyridine (0.33 g).

(4) In methylene chloride (2.0 mL) was dissolved 4-(4-cyano-1,2,3,6-tetrahydropyridin-1-yl)-1-(2,4-dichlorophenyl)-2,3,6-trimethyl-1H-pyrrolo[2,3-b]pyridine (0.19 g), followed by adding thereto concentrated sulfuric acid (0.5 mL) under ice-cooling, and the resulting mixture was slowly heated to room temperature and then stirred overnight. The reaction mixture was separated with ethyl acetate and a saturated aqueous sodium hydrogencarbonate solution, and the aqueous layer was extracted twice with ethyl acetate. The combined organic layer was dried over anhydrous sodium sulfate and the desiccating agent was filtered off, after which the filtrate was concentrated under reduced pressure. The residue was purified by a silica gel column chromatography (silica gel: Wako Gel (C200), eluent: chloroform-methanol=30:1) and the crystals precipitated were washed with ethyl acetate to obtain the title compound (0.10 g).

m.p. 265.0–267.0° C.

Table 11 and Table 12 list the compound obtained in Example 4 and compounds obtained by the same procedure as in Example 4.

EXAMPLE 5

Synthesis of 4-(5-carbamoyl-1,2,3,6-tetrahydropyridin-1-yl)-1-(2,4-dichlorophenyl)-2,3,6-trimethyl-1H-pyrrolo[2,3-b]pyridine (Compound 12-09)

(1) After 60% sodium hydride (an oil dispersion) (79 mg) and a small amount of 35% potassium hydride (an oil dispersion) were washed twice with hexane, tetrahydrofuran (2.0 mL) and diethyl carbonate (0.21 g) were added thereto and the resulting mixture was heated at 80° C. Then, a solution of 1-(2,4-dichlorophenyl)-4-(4-oxopiperidin-1-yl)-2,3,6-trimethyl-1H-pyrrolo[2,3-b]pyridine (0.29 g) synthesized by the same procedure as in Example 4 in tetrahydrofuran (2.0 mL) was added dropwise thereto over a period of 10 minutes, and the resultant mixture was heated under reflux for 1.5 hours. After the reaction mixture was cooled to room temperature, a saturated aqueous ammonium chloride solution was poured into the reaction mixture, which was then extracted three times with ethyl acetate. The combined organic layer was dried over anhydrous sodium sulfate. The desiccating agent was filtered off and the filtrate was concentrated under reduced pressure. The residue was purified by a silica gel column chromatography (silica gel: Wako Gel (C200), eluent: hexane-ethyl acetate=4:1) to obtain 1-(2,4-dichlorophenyl)-4-(3-ethoxy-carbonyl-4-oxopiperidin-1-yl)-2,3,6-trimethyl-1H-pyrrolo[2,3-b]pyridine (0.14 g).

(2) In ethanol (3.0 mL) was dissolved 1-(2,4-dichlorophenyl)-4-(3-ethoxycarbonyl-4-oxopiperidin-1-yl)-2,3,6-trimethyl-1H-pyrrolo[2,3-b]pyridine (0.13 g), and the solution was cooled to −15° C. Then, sodium boro hydride (26 mg) was added thereto and the resulting mixture was stirred overnight while being slowly heated to 0° C. A saturated aqueous ammonium chloride solution was poured into the reaction mixture, which was then extracted three times with ethyl acetate. The combined organic layer was dried over anhydrous sodium sulfate. The desiccating agent was filtered off and the filtrate was concentrated under reduced pressure. The residue was purified by a silica gel column chromatography (silica gel: Wako Gel (C200), eluent: chloroform-methanol=50:1) to obtain 1-(2,4-dichlorophenyl)-4-(3-ethoxycarbonyl-4-hydroxy-piperidin-1-yl)-2,3,6-trimethyl-1H-pyrrolo[2,3-b]pyridine (35 mg).

(3) In methylene chloride (1.5 mL) were dissolved 1-(2,4-dichlorophenyl)-4-(3-ethoxycarbonyl-4-hydroxypiperidin-1-yl)-2,3,6-trimethyl-1H-pyrrolo[2,3-b]pyridine (53 mg), triethylamine (34 mg) and a small amount of 4-dimethylaminopyridine. Methanesulfonyl chloride (25 mg) was added thereto and the resulting mixture was stirred at room temperature for 2 hours. A saturated aqueous sodium hydrogencarbonate solution was poured into the reaction mixture, which was then extracted three times with chloroform. The combined organic layer was dried over anhydrous sodium sulfate. The desiccating agent was filtered off and the filtrate was concentrated under reduced pressure. The residue was dissolved in benzene (1.0 mL), followed by adding thereto 1,8-diazabicyclo[5.4.0]-7-undecene (17 mg), and the resulting mixture was heated under reflux for 1 hour. A saturated aqueous ammonium chloride solution was poured into the reaction mixture, which was then extracted three times with ethyl acetate. The combined organic layer was dried over anhydrous sodium sulfate, after which the desiccating agent was filtered off and the filtrate was concentrated under reduced pressure. The residue was purified by a silica gel column chromatography (silica gel: Wako Gel (C200), eluent: hexane-ethyl acetate=5:1) to obtain 4-(5-ethoxy-carbonyl-1,2,3,6-tetrahydropyridin-1-yl)-1-(2,4-dichlorophenyl)-2,3,6-trimethyl-1H-pyrrolo[2,3-b]pyridine (27 mg).

(4) In ethanol (1.0 mL) was dissolved 4-(5-ethoxycarbonyl-1,2,3,6-tetrahydropyridin-1-yl)-1-(2,4-dichlorophenyl)-2,3,6-trimethyl-1H-pyrrolo[2,3-b]pyridine (27 mg), followed by-adding thereto a 1 M aqueous sodium hydroxide solution (1.0 mL), and the resulting mixture was stirred at room temperature for 8.5 hours. A saturated aqueous ammonium chloride solution was poured into the reaction mixture, which was then extracted three times with chloroform. The combined organic layer was dried over anhydrous sodium sulfate. The desiccating agent was filtered off and the filtrate was concentrated under reduced pressure.

The resultant residue was suspended in a mixed solvent of N,N-dimethylformamide (0.8 mL) and chloroform (0.2 ml), and 1-hydroxybenzotriazole monohydrate (18 mg) and 1-(3-dimethylaminopropyl)-3-ethylcarbodiimide hydrochloride (23 mg) were added thereto. After the resulting mixture was stirred at room temperature for 40 minutes, a few drops of 28% aqueous ammonia solution was added thereto, and the mixture thus obtained was stirred at room temperature for 1.5 hours. A saturated aqueous sodium hydrogen-carbonate solution was poured into the reaction mixture, which was then extracted three times with ethyl acetate. The combined organic layer was dried over anhydrous sodium sulfate. The desiccating agent was filtered off and the filtrate was concentrated under reduced pressure. The residue was purified by a silica gel column chromatography (silica gel: Wako Gel (C200), eluent: hexane-ethyl acetate=1:2) and crystallized from a mixed solvent of diisopropyl ether and ethyl acetate to obtain the title compound (6.0 mg).

Table 12 lists the compound obtained in Example 5.

EXAMPLE 6

Synthesis of 5-(4-carbamoyl-1,2,3,6-tetrahydropyridin-1-yl)-2-(N-ethyl-2,4-dichloroanilino)-4-methylthiazole (Compound 15-01)

(1) After 2-(N-ethyl-2,4-dichloroanilino)-4-methylthiazole hydrochloride (6.0 g) and calcium carbonate (4.6 g) were suspended in a mixed solvent of chloroform (90 mL) and methanol (36 mL), benzyl-trimethylammonium tribromide (7.2 g) was added thereto in small portions. The solids in the reaction mixture were filtered off and the filtrate was concentrated under reduced pressure. The residue was purified by a silica gel column chromatography (silica gel: Wako Gel (C200), eluent: hexane-ethyl acetate=9:1) to obtain 5-bromo-2-(N-ethyl-2,4-dichloroanilino)-4-methyl-thiazole (4.5 g).

(2) A mixture of 5-bromo-2-(N-ethyl-2,4-dichloroanilino)-4-methylthiazole (0.20 g), 5-carbamoyl-1,2,3,6-tetrahydropyridine hydrochloride (178 mg), sodium hydrogencarbonate (94 mg) and ethanol (1.5 mL) was allowed to react in a sealed tube at 120° C. for 3 days. The reaction mixture was separated with water and chloroform and the aqueous layer was extracted with chloroform, after which the combined organic layer was dried over anhydrous sodium sulfate. The desiccating agent was filtered off and the filtrate was concentrated under reduced pressure. The residue was purified by a silica gel column chromatography (silica gel: Wako Gel (C200), eluent: chloroform-methanol=20:1) and then crystallized from diisopropyl ether to obtain the title compound (34 mg).

m.p. 148.0–150.0° C.

Table 15 lists the compound obtained in Example 6.

EXAMPLE 7

Synthesis of 2-{1-[8-(2,4-dichlorophenyl)-2-methylquinolin-4-yl]-piperidin-4-ylidene}-acetamide (Compound 1-22) and 2-{1-[8-(2,4-dichlorophenyl)-2-methylquinolin-4-yl]-1,2,3,6-tetrahydropyridin-4-yl}-acetamide (Compound 1-05)

(1) In a mixture of 1 M hydrochloric acid (26 mL) and tetrahydrofuran (13 mL), 8-(2,4-dichlorophenyl)-4-(1,4-dioxa-8-azaspiro[4.5]dec-8-yl)-2-methylquinoline (2.6 g) obtained by the same procedure as in Example 3, (1) was stirred at room temperature for 2 hours and then at 70° C. for 5.5 hours. The tetrahydrofuran was distilled off under reduced pressure, and the residue was made basic with a 41% aqueous sodium hydroxide solution under ice-cooling and extracted three times with ethyl acetate. The combined organic layer was dried over anhydrous sodium sulfate, after which the desiccating agent was filtered off and the filtrate was concentrated under reduced pressure.

The resultant residue was dissolved in tetrahydrofuran (10 mL) and the resulting solution was added dropwise to a solution of Horner-Emmons reagent that had previously been prepared from ethyl diethyl-phosphonoacetate (2.05 g) and 60% sodium hydride (an oil dispersion) (293 mg) in tetrahydrofuran (10 mL), under ice-cooling over a period of 20 minutes. The ice bath was removed, and the reaction mixture was stirred at room temperature for 30 minutes, quenched with a saturated aqueous ammonium chloride solution, and then extracted twice with ethyl acetate. The combined organic layer was dried over anhydrous sodium sulfate, after which the desiccating agent was filtered off and the filtrate was concentrated under reduced pressure. The resultant residue was purified by a silica gel column chromatography (silica gel: Wako Gel (C200), eluent: hexane-ethyl acetate=9:1) and then crystallized from diisopropyl ether to obtain 8-(2,4-dichlorophenyl)-2-methyl-4-(4-ethoxycarbonyl-methylidenepiperidin-1-yl)quinoline (2.4 g).

(2) In a mixed solvent of 85% potassium hydroxide (1.3 g) and water (1.4 mL)-ethanol (8 mL), 8-(2,4-dichlorophenyl)-2-methyl-4-(4-ethoxycarbonyl-methylidenepiperidin-1-yl)quinoline (2.3 g) was stirred at 80° C. for 1 hour. The reaction mixture was neutralized with 3 M hydrochloric acid under ice-cooling and stirred under ice-cooling for 2 hours and then at room temperature for 30 minutes. The solid precipitated was collected by filtration to obtain a mixture (1.5 g) of 2-{1-[8-(2,4-dichlorophenyl)-2-methylquinolin-4-yl]-piperidin-4-ylidene}acetic acid and 2-{1-[8-(2,4-dichlorophenyl)-2-methylquinolin-4-yl]-1,2,3,6-tetrahydropyridin-4-yl}acetic acid.

(3) A mixture (400 mg) of 2-{1-[8-(2,4-dichlorophenyl)-2-methylquinolin-4-yl]-piperidin-4-ylidene}acetic acid and 2-{1-[8-(2,4-dichlorophenyl)-2-methylquinolin-4-yl]-1,2,3,6-tetrahydropyridin-4-yl}acetic acid, 1-hydroxybenzotriazole monohydrate (215 mg) and 1-(3-dimethylaminopropyl)-3-ethylcarbodiimide hydrochloride (215 mg) were stirred in N,N-dimethyl-formamide (2 ml) at room temperature for 20 minutes. Then, a 28% aqueous ammonia solution (0.075 mL) was added thereto and the resulting mixture was stirred at room temperature for 3 days. The reaction mixture was separated with chloroform and water, and the organic layer was dried over anhydrous sodium sulfate. The desiccating agent was filtered off and the filtrate was concentrated under reduced pressure. The residue was separated and purified twice by a silica gel column chromatography (silica gel: Wako Gel (C200), eluent: chloroform-ethanol=50:1), after which the purified products were crystallized from diethyl ether and diisopropyl ether, respectively, to obtain the title compound 1-22 (109 mg) and the title compound 1-05 (43 mg), respectively.

Compound 1-22: m.p. 225.0–227.0° C.

Compound 1-05: m.p. 160.0–162.0° C.

Table 1 and Table 16 list the compounds obtained in Example 7 and compounds obtained by the same procedure as in Example 7.

EXAMPLE 8

Synthesis of 8-(2,4-dichlorophenyl)-4-(1,4-dioxa-8-azaspiro[4.5]dec-8-yl)-2-methylquinoline (1) After having been washed with hexane, 60% sodium hydride (an oil dispersion) (1.68 g) was suspended in N,N-dimethylformamide (20 mL). To the resulting suspension was added a suspension of 8-bromo-4-hydroxy-2-methylquinoline (10.0 g) in N,N-dimethyl-formamide (35 mL) at room temperature over a period of 10 minutes, followed by stirring at room temperature for 30 minutes. To the resultant solution was added N-phenylbis (trifluoromethanesulfonimide) (15.0 g) all at once, followed by stirring at room temperature for 1 hour.

To the resultant reaction mixture was added 4-piperidone ethylene ketal (11.0 g), and the resulting mixture was stirred at room temperature for 24 hours and heated under reflux at 60° C. for 4 hours and then for 2.5 hours. After 4-piperidone ethylene ketal (5.5 g) was added thereto, the mixture thus obtained was heated under reflux for 3 hours. The reaction mixture was cooled to room temperature, poured into water (200 ml) and then stirred for 24 hours. The solid precipitated was collected by filtration and purified by a silica gel column chromatography (silica gel: Wako Gel (C200), eluent: hexane-ethyl acetate=5:1 to 3:1) to obtain 8-bromo-4-(1,4-dioxa-8-azaspiro[4.5]dec-8-yl)-2-methylquinoline (10.3 g), m.p. 156.0–158.0° C.

(2) Under a nitrogen atmosphere, 8-bromo-4-(1,4-dioxa-6-azaspiro[4.5]dec-8-yl)-2-methylquinoline (10.2 g), 2,4-dichlorophenylboric acid (6.0 g) and sodium carbonate (8.93 g) were suspended in a mixed solvent of deaerated water (24 mL), toluene (12 mL) and ethanol (12 mL), followed by adding thereto tetrakis-(triphenylphosphine)palladium (1.6 g), and the resulting mixture was heated under reflux for 16 hours. The reaction mixture was cooled to room temperature and separated with ethyl acetate and a saturated aqueous ammonium chloride solution. After the aqueous phase was extracted with ethyl acetate, the combined organic phase was dried over anhydrous sodium sulfate. The desiccating agent was filtered off, after which the filtrate was concentrated under reduced pressure and the resultant residue was crystallized from diisopropyl ether. The crystals were collected by filtration and washed with a small amount of diisopropyl ether to obtain the title compound (10.5 g).

m.p. 179.5–181.5° C.

EXAMPLE 9

Synthesis of 8-(2,4-dichlorophenyl)-4-(4-carbamoyl-1,2,3,6-tetrahydropyridin-1-yl)-2-methyl-quinoline (Compound 1-01)

(1) After having been washed with hexane, 60% sodium hydride (an oil dispersion) (1.0 g) was suspended in N-methylpyrrolidone (40 mL). To the suspension was added 8-bromo-4-hydroxy-2-methyl-quinoline (5.0 g) all at once at room temperature, followed by stirring at room temperature for 1 hour. To the resulting solution was added N-phenylbis-(trifluoromethanesulfonimide) (15.0 g) all at once, followed by stirring at room temperature for 1 hour.

To the resultant reaction mixture were added sodium hydrogencarbonate (5.3 g) and 4-carbamoyl-1,2,3,6-tetrahydropyridine hydrochloride (6.8 g), and the resulting mixture was stirred at 130° C. for 30 minutes. After this reaction mixture was cooled to room temperature, water (100 mL) was added thereto, followed by stirring at room temperature for 2 hours. The solid precipitated was collected by filtration and then washed with water to obtain 8-bromo-4-(4-carbamoyl-1,2,3,6-tetrahydropyridin-1-yl)-2-methyl-quinoline (4.8 g).

m.p. 225.0–227.0° C.

(2) Under a nitrogen atmosphere, 8-bromo-2-methyl-4-(4-carbamoyl-1,2,3,6-tetrahydropyridin-1-yl)quinoline (4.7 g), 2,4-dichlorophenylboric acid (2.9 g) and sodium carbonate (4.5 g) were suspended in a mixed solvent of deaerated water (14 mL), toluene (7 mL) and ethanol (7 mL), followed by adding thereto tetrakis(triphenylphosphine)palladium (0.81 g), and the resulting mixture was heated under reflux for 5 hours. The reaction mixture was cooled to room temperature and stirred at room temperature for 3 hours. The solid precipitated was collected by filtration and washed with a water-ethanol (2:1) mixed solvent (30 mL) and then ethanol (30 mL) to obtain the title compound (4.7 g).

Table 1 lists the compound obtained in

Example 9.

EXAMPLE 10

Synthesis of 8-(2,4-dichlorophenyl)-4-(4-isopropyloxycarbonyl-1,2,3,6-tetrahydropyridin-1-yl)-2-methylquinoline (Compound 1-14)

(1) After having been washed with hexane, 60% sodium hydride (an oil dispersion) (1.0 g) was suspended in N-methylpyrrolidone (30 mL). To the suspension was added 8-bromo-4-hydroxy-2-methyl-quinoline (5.0 g) all at once at room temperature, followed by stirring at room temperature for 1 hour.

To the resulting solution was added N-phenylbis-(trifluoromethanesulfonimide) (9.0 g) all at once, followed by stirring at room temperature for 1 hour. To the resultant reaction mixture was added 4-isopropyloxycarbonyl-1,2,3,6-tetrahydropyridine (8.5 g), and the resulting mixture was stirred overnight at room temperature. This reaction mixture was poured into a mixture of water and ethyl acetate to be separated. After the aqueous phase was extracted with ethyl acetate, the combined organic phase was dried over anhydrous sodium sulfate. The desiccating agent was filtered off and the filtrate was concentrated under reduced pressure. The residue was purified by a silica gel column chromatography (silica gel: Wako Gel (C200), eluent: hexane-ethyl acetate=9:1), and the solid thus obtained was washed with a mixture of diisopropyl ether and hexane to obtain 8-bromo-4-(4-isopropyloxycarbonyl-1,2,3,6-tetrahydropyridin-1-yl)-2-methylquinoline (6.0 g).

m.p. 130.0–131.0° C.

(2) Under a nitrogen atmosphere, 8-bromo-4-(4-isopropyloxycarbonyl-1,2,3,6-tetrahydropyridin-1-yl)-2-methylquinoline (5.9 g), 2,4-dichlorophenylboric acid (3.2 q) and sodium carbonate (4.8 g) were suspended in a mixed solvent of deaerated water (15 mL), toluene (7.5 mL) and ethanol (7.5 mL), followed by adding thereto tetrakis (triphenylphosphine)palladium (0.88 g), and the resulting mixture was heated under reflux for 5 hours. The reaction mixture was cooled to room temperature to be separated. After the aqueous phase was extracted with ethyl acetate, the combined organic phase was dried over anhydrous sodium sulfate. The desiccating agent was filtered off, after which the filtrate was concentrated under reduced pressure and the resultant residue was crystallized from diisopropyl ether. The crystals were collected by filtration and washed with a small amount of diisopropyl ether to obtain the title compound (5.3 g).

m.p. 131.0–133.0° C.

Table 1 lists the compound obtained in Example 10.

EXAMPLE 11

Synthesis of 8-(2,4-dichlorophenyl)-4-(4-carboxy-1,2,3,6-tetrahydropyridin-1-yl)-2-methyl-quinoline (Compound 1-11)

In concentrated hydrochloric acid (10 mL) was suspended 8-(2,4-dichlorophenyl)-4-(4-carbamoyl-1,2,3,6-tetrahydropyridin-1-yl)-2-methylquinoline (0.10 g), and the suspension was heated under reflux for 1 hour. After the reaction mixture was concentrated under reduced pressure, 28% aqueous ammonia (2 mL) was added thereto, followed by concentration under reduced pressure. The residue was purified by a silica gel column chromatography (silica gel: Wako Gel (C200), eluent: chloroform-methanol=20:1 to 10:1), and the solid precipitated was washed with ethyl acetate to obtain the title compound (74 mg).

m.p. 218.0–220.0° C.

Table 1 lists the compound obtained in Example 11.

TABLE 1*[1]

[Structure: quinoline/quinazoline core with substituents R5, R6, R7, Ar, A, E, R4]

| Com. No. | Ex. No. | A | E | R⁴ | R⁵ | R⁶ | R⁷ | Ar | Melting point (° C.) (solvent for crystallization) |
|---|---|---|---|---|---|---|---|---|---|
| 1-01 | 1, 3, 9 | 1-methyl-1,2,3,6-tetrahydropyridin-4-yl with H₂NCO- at 4-position | CH | CH₃ | H | H | H | 2,4-dichlorophenyl | 263.5–265.5(MeOH) |
| 1-02 | 2 | 1-methyl-1,2,3,6-tetrahydropyridin-4-yl with H₂NCO- | CH | CH₃ | H | H | H | 2,3,5-trimethylphenyl | 220.5–222.5(AcOEt) |
| 1-03 | 2 | 1-methyl-1,2,3,6-tetrahydropyridin-4-yl with H₂NCO- | CH | CH₃ | H | H | H | 2,4-dimethoxyphenyl | 242.0–244.0(MeOH) |
| 1-04 | 2 | 1-methyl-1,2,3,6-tetrahydropyridin-4-yl with H₂NCO- | N | CH₃ | H | H | H | 2,4-dichlorophenyl | 220.0–222.0(Et₂O) |
| 1-05 | 7 | H₂NCO-CH₂-(1-methyl-1,2,3,6-tetrahydropyridin-4-yl) | CH | CH₃ | H | H | H | 2,4-dichlorophenyl | 160.0–162.0(IPE) |
| 1-06 | 1 | 1-methyl-1,2,3,6-tetrahydropyridin-4-yl with H₂NCO- | CH | CH₃ | H | H | H | 2-chloro-4-trifluoromethylphenyl | 235.0–236.0(MeOH) |
| 1-07 | 1 | 1-methyl-1,2,3,6-tetrahydropyridin-4-yl with H₂NCO- | CH | CH₃ | H | H | H | 2-chloro-4-trifluoromethoxyphenyl | 215.0–216.0(MeOH) |
| 1-08 | 1 | 1-methyl-1,2,3,6-tetrahydropyridin-4-yl with H₂NCO- | CH | CH₃ | H | H | H | 2,6-dimethoxypyridin-3-yl | 228.0–230.0(MeOH) |

TABLE 1*¹-continued

| Com. No. | Ex. No. | A | E | R⁴ | R⁵ | R⁶ | R⁷ | Ar | Melting point (° C.) (solvent for crystallization) |
|---|---|---|---|---|---|---|---|---|---|
| 1-09 | 1 | H₂NCO-（1-methyl-1,2,3,6-tetrahydropyridin-4-yl） | CH | CH₃ | H | Cl | H | 2,4-diClC₆H₃ | 256.0–258.0(MeOH) |
| 1-10 | 1 | H₂NCO-（1-methyl-1,2,3,6-tetrahydropyridin-4-yl） | CH | CH₃ | H | CH₃ | H | 2,4-diClC₆H₃ | 252.0–254.0(MeOH) |
| 1-11 | 11 | HOCO-（1-methyl-1,2,3,6-tetrahydropyridin-4-yl） | CH | CH₃ | H | H | H | 2,4-diClC₆H₃ | 218.0–220.0(AcOEt) |
| 1-12 | 1 | H₂NCO-（1-methyl-1,2,3,6-tetrahydropyridin-4-yl） | CH | CH₃ | H | F | H | 2,4-diClC₆H₃ | 273.0–275.0(MeOH) |
| 1-13 | 1 | H₂NCO-（1-methyl-1,2,3,6-tetrahydropyridin-4-yl） | CH | CH₃ | H | OCF₃ | H | 2,4-diClC₆H₃ | 235.0–236.0(MeOH) |
| 1-14 | 10 | iPrOCO-（1-methyl-1,2,3,6-tetrahydropyridin-4-yl） | CH | CH₃ | H | H | H | 2,4-diClC₆H₃ | 131.0–133.0(IPE/hexane) |
| 1-15 | 2 | H₂NCO-（1-methyl-1,2,5,6-tetrahydropyridin-3-yl） | CH | CH₃ | H | H | H | 2,4-diClC₆H₃ | 230.0–232.0(AcOEt) |
| 1-16 | 2 | H₂NCO-（1-methyl-1,2,5,6-tetrahydropyridin-3-yl） | CH | CH₃ | H | H | H | 2,4,6-triMeC₆H₂ | 144.5–146.5(AcOEt) |

TABLE 1*¹-continued

| Com. No. | Ex. No. | A | E | R⁴ | R⁵ | R⁶ | R⁷ | Ar | Melting point (° C.) (solvent for crystallization) |
|---|---|---|---|---|---|---|---|---|---|
| 1-17 | 2 | H₂NCO-(N-methyl-tetrahydropyridinyl) | CH | CH₃ | H | H | H | 4-CF₃-phenyl | 140.5–142.5(Et₂O) |
| 1-18 | 2 | H₂NCO-(N-methyl-tetrahydropyridinyl) | CH | CH₃ | H | H | H | 2-OCH₃,4-OCH₃-phenyl | 185.0–187.0(EtOH) |
| 1-19 | 2 | H₂NCO-(N-methyl-tetrahydropyridinyl) | N | CH₃ | H | H | H | 2,4-diCl-phenyl | Amorphous*² |
| 1-20 | 1 | H₂NCO-(N-methyl-tetrahydropyridinyl) | CH | CH₃ | H | F | H | 2,4-diCl-phenyl | 237.0–238.0(MeOH) |
| 1-21 | 1 | H₂NCO-(N-methyl-tetrahydropyridinyl) | CH | CH₃ | H | OCF₃ | H | 2,4-diCl-phenyl | 170.0–173.0(EtOH)*³ |
| 1-22 | 7 | H₂NCO-CH=(N-methyl-piperidinyl) | CH | CH₃ | H | H | H | 2,4-diCl-phenyl | 225.0–227.0(Et₂O) |
| 1-23 | 1 | H₂NCO-(N-methyl-tetrahydropyridinyl, 4-yl) | CH | CH₃ | H | N(CH₃)₂ | H | 2,4-diCl-phenyl | 202.0–204.0(EtOH) |
| 1-24 | 1 | H₂NCO-(N-methyl-tetrahydropyridinyl) | CH | CH₃ | H | N(CH₃)₂ | H | 2,4-diCl-phenyl | 187.0–189.0(IPA/AcOEt)*³ |

TABLE 1*1-continued

[Structure: quinoline core with R5, R6, R7 on benzene ring, Ar at 8-position, A at 4-position, E in ring, R4 at 2-position]

| Com. No. | Ex. No. | A | E | R⁴ | R⁵ | R⁶ | R⁷ | Ar | Melting point (° C.) (solvent for crystallization) |
|---|---|---|---|---|---|---|---|---|---|
| 1-25 | 1 | H₂NCO-(4-tetrahydropyridinyl-N-Me) | CH | CH₃ | F | H | H | 2,4-dichlorophenyl | 244.0–246.0(EtOH) |
| 1-26 | 1 | H₂NCO-(3-tetrahydropyridinyl-N-Me) | CH | CH₃ | F | H | H | 2,4-dichlorophenyl | 214.0–216.0(EtOH) |
| 1-27 | 1 | H₂NCO-(4-tetrahydropyridinyl-N-Me) | CH | H | H | H | H | 2,4-dichlorophenyl | >235 (decomposed) (EtOH) |
| 1-28 | 1 | H₂NCO-(3-tetrahydropyridinyl-N-Me) | CH | H | H | H | H | 2,4-dichlorophenyl | 220.5–222.5(EtOH) |
| 1-29 | 1 | H₂NCO-(4-tetrahydropyridinyl-N-Me) | CH | NH₂ | H | H | H | 2,4-dichlorophenyl | >230(decomposed) (MeOH) |
| 1-30 | 1 | H₂NCO-(3-tetrahydropyridinyl-N-Me) | CH | NH₂ | H | H | H | 2,4-dichlorophenyl | 155.0–158.5(IPA/Et₂O) |

*1Com. No. = compound number, Ex. No. = example number, solvent for crystallization; MeOH = methanol, EtOH = ethanol, AcOEt = ethyl acetate, Et₂O = diethyl ether

*2 1H NMR (200 MHz, CDCl₃); δ 2.41(3H, 5), 2.48–2.66(2H, m), 3.72–3.95(2H, m), 4.34–4.46(2H, m), 6.76–6.87(1H, m), 7.05(1H, br, 5), 7.42(1H, d, J=8.4Hz), 7.47–7.63(3H, m), 7.68(1H, dd, J=1.3, 7.3Hz), 7.72(1H, d, J=1.8Hz), 8.04(1H, dd, J=1.3, 8.4Hz).

MS(ES, Pos); 435(M + Na)⁺, 437(M + Na + 2)⁺, 439(M + Na + 4)⁺

*3HCl salt

TABLE 2*¹

[Structure: pyrido-pyrimidine core with R⁶, R⁵, A, E, R⁴, Ar substituents]

| Com. No. | Ex. No. | A | E | R⁴ | R⁵ | R⁶ | Ar | Melting point (° C.) (solvent for crystallization) |
|---|---|---|---|---|---|---|---|---|
| 2-01 | 2 | H₂NCO-[1,2,3,6-tetrahydropyridin-4-yl, N-methyl] | N | CH₃ | H | H | 2,4-dichlorophenyl | 221.0–223.0(AcOEt) |
| 2-02 | 1 | H₂NCO-[1,2,3,6-tetrahydropyridin-4-yl, N-methyl] | CH | CH₃ | H | H | 2,4-dichlorophenyl | 277.0–279.0(AcOEt) |
| 2-03 | 2 | H₂NCO-[1,2,5,6-tetrahydropyridin-3-yl, N-methyl] | N | CH₃ | H | H | 2,4-dichlorophenyl | 100.0–102.0(IPE) |

*¹Com. No. = compound number, Ex. No. = example number, solvent for crystallization; AcOEt = ethyl acetate, IPE = diisopropyl ether

TABLE 3*¹

[Structure: pyrazolo[1,5-a]pyrimidine core with R⁵, Ar, A, E, R⁴ substituents]

| Com. No. | Ex. No. | A | E | R⁴ | R⁵ | Ar | Melting point (° C.) (solvent for crystallization) |
|---|---|---|---|---|---|---|---|
| 3-01 | 2 | H₂NCO-[1,2,3,6-tetrahydropyridin-4-yl, N-methyl] | CH | CH₃ | CH₃ | 2,4,6-trimethylphenyl | 245.0–247.0(AcOEt/IPE) |
| 3-02 | 2 | H₂NCO-[1,2,3,6-tetrahydropyridin-4-yl, N-methyl] | N | CH₃ | CH₃ | 2,4,6-trimethylphenyl | 245.0–247.0(AcOEt/IPE) |

TABLE 3*¹-continued
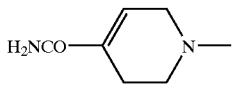
| Com. No. | Ex. No. | A | E | R⁴ | R⁵ | Ar | Melting point (° C.) (solvent for crystallization) |
|---|---|---|---|---|---|---|---|
| 3-03 | 2 | 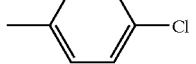 | CH | CH₃ | CH₃ | 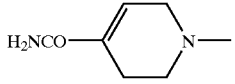 | 252.0–254.0(AcOEt) |
| 3-04 | 2 | 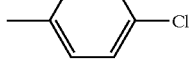 | N | CH₃ | CH₃ | 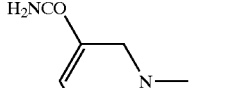 | 255.0–257.0(AcOEt) |
| 3-05 | 2 | 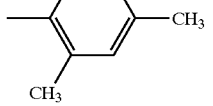 | CH | CH₃ | CH₃ | 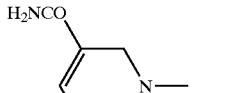 | 187.0–189.0(AcOEt/IPE) |
| 3-06 | 2 | 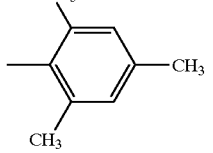 | N | CH₃ | CH₃ | 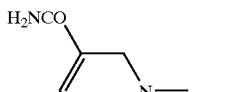 | 145.0–147.0(EtOH/AcOEt)*² |
| 3-07 | 2 |  | CH | CH₃ | CH₃ | 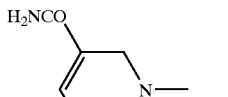 | 150.0–152.0(AcOEt) |
| 3-08 | 2 | 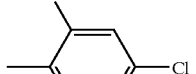 | N | CH₃ | CH₃ | 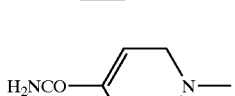 | 209.0–211.0(AcOEt) |
| 3-09 | 2 | 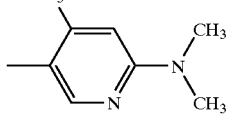 | CH | CH₃ | CH₃ | | 245.0–247.0(AcOEt/IPE) |

TABLE 3*1-continued

Structure:

$$R^5, Ar, A, E, R^4 \text{ substituted pyrazolo-pyrimidine core}$$

| Com. No. | Ex. No. | A | E | R⁴ | R⁵ | Ar | Melting point (° C.) (solvent for crystallization) |
|---|---|---|---|---|---|---|---|
| 3-10 | 2 | 3-(aminocarbonyloxy)-1-methyl-1,2,5,6-tetrahydropyridin-3-yl (H₂NCO-O-) | CH | CH₃ | CH₃ | 6-(N,N-dimethylamino)-3,4-dimethylpyridin-2-yl | 253.0–255.0(AcOEt/IPE) |

*¹Com. No. = compound number, Ex. No. = example number, solvent for crystallization; EtOH = ethanol, AcOEt = ethyl acetate, IPE = diisopropyl ether
*²HCl salt

TABLE 4*1

Structure:

$$R^9, R^5, Ar, A, E, R^4 \text{ substituted pyrrolo-pyridine core}$$

| Com. No. | Ex. No. | A | E | R⁴ | R⁵ | R⁹ | Ar | Melting point (° C.) (solvent for crystallization) |
|---|---|---|---|---|---|---|---|---|
| 4-01 | 2 | 4-(aminocarbonyloxy)-1-methylpiperidin-4-yl (H₂NCO-O-) | N | CH₃ | H | CH₃ | 2,4-dichlorophenyl | Amorphous*² |
| 4-02 | 2 | 3-(aminocarbonyloxy)-1-methyl-1,2,5,6-tetrahydropyridin-3-yl (H₂NCO-O-) | N | CH₃ | H | CH₃ | 2,4-dichlorophenyl | 169.0–171.0(AcOEt/Et₂O) |

*¹Com. No. = compound number, Ex. No. = example number, solvent for crystallization; AcOEt = ethyl acetate, Et₂O = diethyl ether
*²¹H NMR (200 MHz, CDCl₃); δ 2.57–2.75(2H, m), 2.67(3H, s), 3.55(2H, t, J=5.7Hz), 4.01(3H, s), 4.08–4.18(2H, m), 6.70–6.82 (1H, m), 7.35(1H, dd, J=2.1, 8.6Hz), 7.49(1H, d, J=2.1Hz), 7.70(1H, S), 8.09(1H, d, J=8.6Hz).
MS(ES, Pos.); 416(M + 1)⁺, 418(M + 3)⁺

TABLE 5*1

| Com. No. | Ex. No. | A | E | R⁴ | R⁹ | Ar | Melting point (° C.) (solvent for crystallization) |
|---|---|---|---|---|---|---|---|
| 5-01 | 2 | H₂NCO-[piperidine] | N | CH₃ | CH₃ | 2,4-dichlorophenyl | 267.0–269.0(AcOEt) |
| 5-02 | 2 | H₂NCO-[tetrahydropyridine] | N | CH₃ | CH₃ | 2,4-dichlorophenyl | 165.0–167.0(AcOEt) |

*¹Com. No. = compound number, Ex. No. = example number, solvent for crystallization; AcOEt = ethyl acetate

TABLE 6*1

| Com. No. | Ex. No. | A | E | R⁴ | R⁹ | Ar | Melting point (° C.) (solvent for crystallization) |
|---|---|---|---|---|---|---|---|
| 6-01 | 2 | H₂NCO-[piperidine] | N | CH₃ | CH₃ | 2,4-dichlorophenyl | 221.0–223.0(Et₂O) |
| 6-02 | 2 | H₂NCO-[tetrahydropyridine] | N | CH₃ | CH₃ | 2,4-dichlorophenyl | 209.0–211.0(Et₂O) |

*¹Com. No. = compound number, Ex. No. = example number, solvent for crystallization; Et₂O = diethyl ether

TABLE 7*[1]

[Structure: pyrazolo-pyrimidine core with R⁹ on N, Ar at 3-position, A at 7-position, E in ring, R⁴ at 5-position]

| Com. No. | Ex. No. | A | E | R⁴ | R⁹ | Ar | Melting point (° C.) (solvent for crystallization) |
|---|---|---|---|---|---|---|---|
| 7-01 | 2 | H₂NCO-(tetrahydropyridin-4-yl)-N— | N | CH₃ | CH₃ | 2,4-dichlorophenyl | 266.0–268.0(AcOEt) |
| 7-02 | 1 | H₂NCO-(tetrahydropyridin-4-yl)-N— | CH | CH₃ | CH₃ | 2,4-dichlorophenyl | 231.0–233.0(AcOEt) |
| 7-03 | 2 | H₂NCO-(tetrahydropyridin-3-yl)-N— | N | CH₃ | CH₃ | 2,4-dichlorophenyl | 211.0–213.0(AcOEt) |

*[1]Com. No. = compound number, Ex. No. = example number, solvent for crystallization; AcOEt = ethyl acetate, Et₂O = diethyl ether

TABLE 8*[1]

[Structure: thiazolo-pyrimidine-2-thione core with Ar on N, A at 7-position, E in ring, R⁴ at 5-position]

| Com. No. | Ex. No. | A | E | R⁴ | Ar | Melting point (° C.) (solvent for crystallization) |
|---|---|---|---|---|---|---|
| 8-01 | 2 | H₂NCO-(tetrahydropyridin-4-yl)-N— | N | CH₃ | 2,4-dichlorophenyl | 283.0–285.0(AcOEt) |
| 8-02 | 2 | H₂NCO-(tetrahydropyridin-3-yl)-N— | N | CH₃ | 2,4-dichlorophenyl | 186.0–188.0(AcOEt/IPE) |

*[1]Com. No. = compound number, Ex. No. = example number, solvent for crystallization; AcOEt = ethyl acetate, IPE = diisopropyl ether

TABLE 9*[1]

[Structure: isoxazoline fused to pyrimidine with substituents A, E, R⁴, Ar]

| Com. No. | Ex. No. | A | E | R⁴ | Ar | Melting point (° C.) (solvent for crystallization) |
|---|---|---|---|---|---|---|
| 9-01 | 2 | H₂NCO-[tetrahydropyridine]-N— | N | CH₃ | 2,4-dichlorophenyl | 191.0–193.0(AcOEt/IPE) |
| 9-02 | 2 | H₂NCO-[tetrahydropyridine]-N— | N | CH₃ | 2,4-dichlorophenyl | 217.0–219.0(AcOEt) |

*[1]Com. No. = compound number, Ex. No. = example number, solvent for crystallization; AcOEt = ethyl acetate, IPE = diisopropyl ether

TABLE 10*[1]

[Structure: pyrrolopyrimidine with substituents A, E, R⁴, R⁵, R⁶, Ar]

| Com. No. | Ex. No. | A | E | R⁴ | R⁵ | R⁶ | Ar | Melting point (° C.) (solvent for crystallization) |
|---|---|---|---|---|---|---|---|---|
| 10-01 | 2 | H₂NCO-[tetrahydropyridine]-N— | CH | CH₃ | H | H | 2,4-dichlorophenyl | 242.0–244.0(Et₂O) |
| 10-02 | 2 | H₂NCO-[tetrahydropyridine]-N— | CH | CH₃ | H | H | 2,4-dichlorophenyl | 208.0–210.0(AcOEt/IPE) |

*[1]Com. No. = compound number, Ex. No. = example number, solvent for crystallization; AcOEt = ethyl acetate, Et₂O = diethyl ether, IPE = diisopropyl ether

TABLE 11[*1]
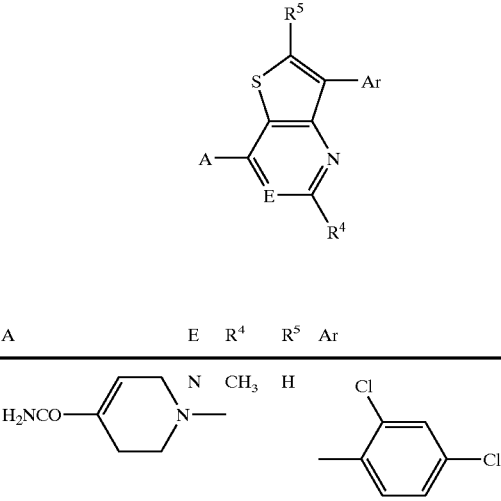
| Com. No. | Ex. No. | A | E | R[4] | R[5] | Ar | Melting point (° C.) (solvent for crystallization) |
|---|---|---|---|---|---|---|---|
| 11-01 | 2 | 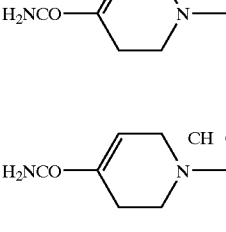 | N | CH$_3$ | H | 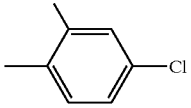 | 220.0—222.0(THF/hexane) |
| 11-02 | 4 | 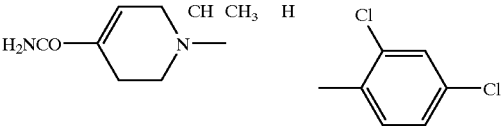 | CH | CH$_3$ | H | 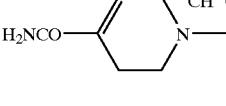 | 238.0–240.0(CHCl$_3$/MeOH) |
| 11-03 | 2 | 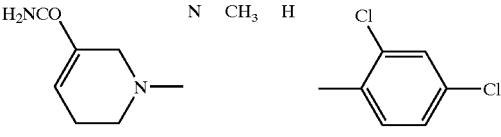 | N | CH$_3$ | H | 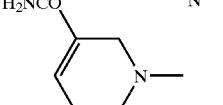 | 216.0–218.0(THF/hexane) |
*[1]Com. No. = compound number, Ex. No. = example number, solvent for crystallization; MeOH = methanol, THF = tetrahydrofuran
TABLE 12[*1]
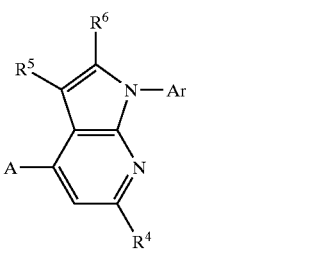
| Com. No. | Ex. No. | A | R[4] | R[5] | R[6] | Ar | Melting point (° C.) (solvent for crystallization) |
|---|---|---|---|---|---|---|---|
| 12-01 | 4 | 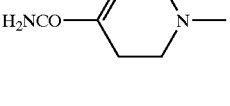 | CH$_3$ | CH$_3$ | CH$_3$ | 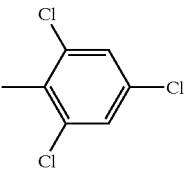 | 265.0–267.0(ACOEt) |
| 12-02 | 4 | 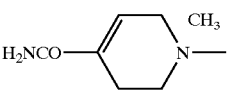 | CH$_3$ | CH$_3$ | CH$_3$ | | 273.0–275.0(ACOEt) |

TABLE 12*¹-continued

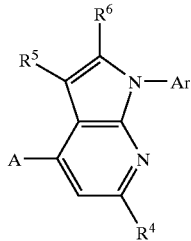

| Com. No. | Ex. No. | A | R⁴ | R⁵ | R⁶ | Ar | Melting point (° C.) (solvent for crystallization) |
|---|---|---|---|---|---|---|---|
| 12-03 | 4 | H₂NCO-[tetrahydropyridine-CH₃, N-CH₃] | CH₃ | CH₃ | CH₃ | 3,5-Cl₂-4-CH₃-phenyl... (2,6-dichloro-4-bromophenyl with methyl) | 267.0–269.0(ACOEt) |
| 12-04 | 4 | H₂NCO-[tetrahydropyridine-CH₃, N-CH₃] | CH₃ | CH₃ | CH₃ | 3-Br-5-SCH₃-4-CH₃-phenyl-Br | 208.0–210.0(ACOEt) |
| 12-05 | 4 | H₂NCO-[tetrahydropyridine-CH₃, N-CH₃] | CH₃ | CH₃ | CH₃ | 3-Br-5-OCH₃-4-CH₃-phenyl-Br | 170.0–172.0(ACOEt/IPE) |
| 12-06 | 4 | H₂NCO-[tetrahydropyridine-CH₃, N-CH₃] | CH₃ | CH₃ | CH₃ | 3,5-Br₂-4-CH₃-phenyl | 162.0–164.0(ACOEt) |
| 12-07 | 4 | H₂NCO-[tetrahydropyridine-CH₃, N-CH₃] | CH₃ | CH₃ | CH₃ | 3-Br-4-CH₃-5-CF₃... (2-Br-4-CF₃-phenyl) | 249.0–251.0(ACOEt) |
| 12-08 | 4 | H₂NCO-[tetrahydropyridine-CH₃, N-CH₃] | CH₃ | CH₃ | CH₃ | 3,5-Br₂-4-CH₃-CF₃-phenyl | 203.0–205.0(CHCl₃/IPE) |

TABLE 12*¹-continued

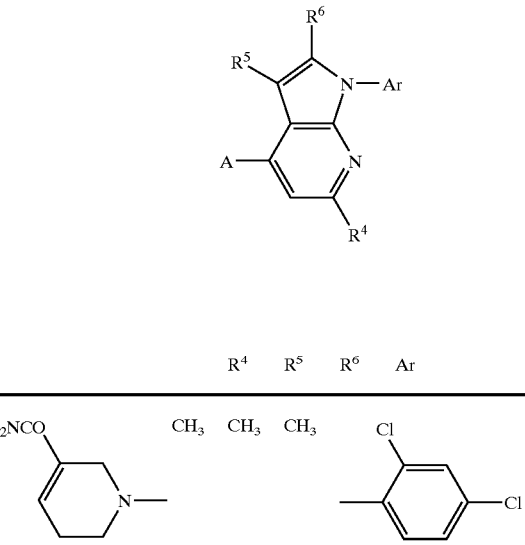

| Com. No. | Ex. No. | A | R⁴ | R⁵ | R⁶ | Ar | Melting point (° C.) (solvent for crystallization) |
|---|---|---|---|---|---|---|---|
| 12-09 | 5 | 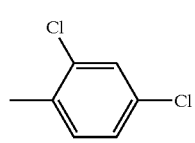 | CH₃ | CH₃ | CH₃ | 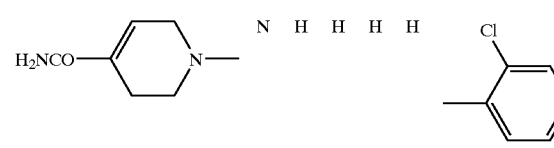 | Amorphous*² |

*¹Com. No. = compound number, Ex. No. = example number, solvent for crystallization; AcOEt = ethyl acetate, IPE = diisopropyl ether

*²1H NMR (200 MHz, CDCl3); δ 2.06(3H, s), 2.40(3H, s), 2.45(3H, br, s), 2.48–2.60(2H, m), 3.21–3.43(2H, m), 3.86–3.96(2H, m), 6.54(1H, s), 6.70–6.77(1H, m), 7.29(1H, d, J=8.5Hz), 7.39(1H, dd, J=2.3, 8.5Hz), 7.57(1H, d, J=2.3Hz).

MS(ES, Pos); 429(M + 1)⁺, 431(M + 3)⁺

TABLE 13*¹

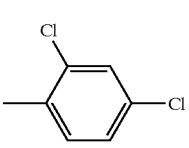

| Com. No. | Ex. No. | A | E | R⁵ | R⁶ | R⁷ | R⁸ | Ar | Melting point (° C.) (solvent for crystallization) |
|---|---|---|---|---|---|---|---|---|---|
| 13-01 | 2 | 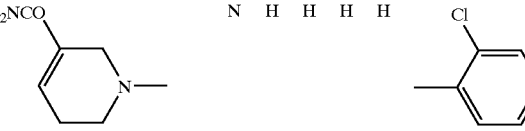 | N | H | H | H | H | 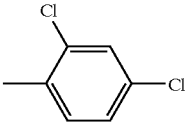 | 294.0–296.0(THF/CHCl₃) |
| 13-02 | 2 | 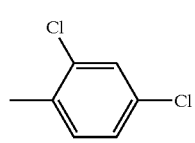 | N | H | H | H | H | 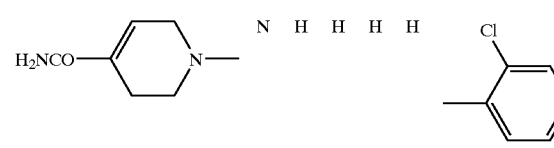 | 133.0–135.0(AcOEt/IPE) |

*¹Com. No. = compound number, Ex. No. = example number, solvent for crystallization; AcOEt = ethyl acetate, IPE = diisopropyl ether, THF = tetrahydrofuran

TABLE 14*[1]

| Com. No. | Ex. No. | A | $R^4$ | $R^5$ | $R^9$ | Ar | Melting point (° C.) (solvent for crystallization) |
|---|---|---|---|---|---|---|---|
| 14-01 | 3 | H₂NCO-[tetrahydropyridine]-N— | $CH_3$ | $CH_3$ | H | 2,4,6-trichlorophenyl | 241.0–243.0(AcOEt/IPE) |

*[1]Com. No. = compound number, Ex. No. = example number, solvent for crystallization; AcOEt = ethyl acetate, IPE = diisopropyl ether

TABLE 15*[1]

| Com. No. | Ex. No. | A | $R^4$ | $R^9$ | Ar | Melting point (° C.) (solvent for crystallization) |
|---|---|---|---|---|---|---|
| 15-01 | 6 | H₂NCO-[tetrahydropyridine]-N— | $CH_3$ | $CH_2CH_3$ | 2,4-dichlorophenyl | 148.0–150.0(IPE) |

*[1]Com. No. = compound number, Ex. No. = example number, solvent for crystallization; IPE = diisopropyl ether

TABLE 16*[1]

| Com. No. | Ex. No. | A | E | $R^4$ | $R^9$ | Ar | Melting point (° C.) (solvent for crystallization) |
|---|---|---|---|---|---|---|---|
| 16-01 | 2 | H₂NCO-[tetrahydropyridine]-N— | CH | $CH_3$ | $CH_2CH_3$ | 2-methyl-5-isopropyl-(methylthio)phenyl | 100.0–102.0(Et₂O/hexane) |

TABLE 16*[1]-continued

| Com. No. | Ex. No. | A | E | R[4] | R[9] | Ar | Melting point (° C.) (solvent for crystallization) |
|---|---|---|---|---|---|---|---|
| 16-02 | 2 | CH₃NHCO-[1-methyl-1,2,3,6-tetrahydropyridin-4-yl] | CH | CH₃ | CH₂CH₃ | 2-CH₃S-4-isopropyl-phenyl (CH₃ at position) | 211.0–213.0(Et₂O) |
| 16-03 | 2 | PhNHCO-[1-methyl-1,2,3,6-tetrahydropyridin-4-yl] | CH | CH₃ | CH₂CH₃ | 2-CH₃S-4-isopropyl-phenyl | 140.0–142.0(AcOEt) |
| 16-04 | 2 | morpholino-CO-[1-methyl-1,2,3,6-tetrahydropyridin-4-yl] | CH | CH₃ | CH₂CH₃ | 2-CH₃S-4-isopropyl-phenyl | 138.0–140.0(Et₂O/hexane) |
| 16-05 | 7 | CH₃OCO-CH=[1-methylpiperidin-4-ylidene] | CH | CH₃ | CH₂CH₃ | 2-CH₃S-4-isopropyl-phenyl | oilz*[2] |
| 16-06 | 7 | CH₃CH₂OCO-CH=[1-methylpiperidin-4-ylidene] | CH | CH₃ | CH₂CH₃ | 2-CH₃S-4-isopropyl-phenyl | oil*[3] |
| 16-07 | 7 | CH₃CH₂OCO-CH=[1-methylpiperidin-4-ylidene] | CH | CH₃ | cyclopropylmethyl | 2-CH₃S-4-isopropyl-phenyl | oil*[4] |
| 16-08 | 7 | CH₃CH₂OCO-CH=[1-methylpiperidin-4-ylidene] | CH | CH₃ | CH₂CH=CHCH₃ | 2-CH₃S-4-isopropyl-phenyl | oil*[5] |
| 16-09 | 7 | CH₃CH₂OCO-CH=[1-methylpiperidin-4-ylidene] | CH | CH₃ | CH₂C≡CH | 2-CH₃S-4-isopropyl-phenyl | oil*[6] |
| 16-10 | 7 | CH₃CH₂OCO-C(CH₃)=[1-methylpiperidin-4-ylidene] | CH | CH₃ | CH₂CH₃ | 2-CH₃S-4-isopropyl-phenyl | oil*[7] |

TABLE 16*1-continued

Structure: 2-(N(R9)-Ar)-4-A-6-R4 pyrimidine/triazine (E)

| Com. No. | Ex. No. | A | E | R4 | R9 | Ar | Melting point (° C.) (solvent for crystallization) |
|---|---|---|---|---|---|---|---|
| 16-11 | 7 | HOCO-CH=(1-methylpiperidin-4-ylidene) | CH | CH$_3$ | CH$_2$CH$_3$ | 2-(CH$_3$S)-4-methyl-5-isopropylphenyl | oil*8 |
| 16-12 | 7 | NC-CH=(1-methylpiperidin-4-ylidene) | CH | CH$_3$ | CH$_2$CH$_3$ | 2-(CH$_3$S)-4-methyl-5-isopropylphenyl | oil*9 |
| 16-13 | 7 | H$_2$NCO-CH=(1-methylpiperidin-4-ylidene) | CH | CH$_3$ | CH$_2$CH$_3$ | 2-(CH$_3$S)-4-methyl-5-isopropylphenyl | oil*10 |
| 16-14 | 7 | CH$_3$NHCO-CH=(1-methylpiperidin-4-ylidene) | CH | CH$_3$ | CH$_2$CH$_3$ | 2-(CH$_3$S)-4-methyl-5-isopropylphenyl | oil*11 |
| 16-15 | 7 | (CH$_3$)$_2$NCO-CH=(1-methylpiperidin-4-ylidene) | CH | CH$_3$ | CH$_2$CH$_3$ | 2-(CH$_3$S)-4-methyl-5-isopropylphenyl | oil*12 |
| 16-16 | 7 | PhCH$_2$NHCO-CH=(1-methylpiperidin-4-ylidene) | CH | CH$_3$ | CH$_2$CH$_3$ | 2-(CH$_3$S)-4-methyl-5-isopropylphenyl | oil*13 |
| 16-17 | 7 | (pyrrolidin-1-yl)CO-CH=(1-methylpiperidin-4-ylidene) | CH | CH$_3$ | CH$_2$CH$_3$ | 2-(CH$_3$S)-4-methyl-5-isopropylphenyl | oil*14 |
| 16-18 | 7 | (morpholin-4-yl)CO-CH=(1-methylpiperidin-4-ylidene) | CH | CH$_3$ | CH$_2$CH$_3$ | 2-(CH$_3$S)-4-methyl-5-isopropylphenyl | oil*15 |

TABLE 16*¹-continued

| Com. No. | Ex. No. | A | E | $R^4$ | $R^9$ | Ar | Melting point (° C.) (solvent for crystallization) |
|---|---|---|---|---|---|---|---|
| 16-19 | 2 | H₂NCO-(N-methyl tetrahydropyridine) | N | CH₃ | CH₂CH₃ | 2-bromo-4-isopropyl-phenyl | 117.0–119.0(IPE) |

*¹Com. No. = compound number, Ex. No. = example number, solvent for crystallization; AcOEt = ethyl acetate, Et2O = diethyl ether, IPE = diisopropyl ether

*²¹H NMR (200 MHz, CDCl₃); δ 1.20(3H, t, J=7.0Hz), 1.29(6H, d, J=6.8Hz), 2.12–2.34(2H, m), 2.20(3H, s), 2.36(3H, s), 2.80–3.04(3H, m), 3.30–4.39 (6H, m), 3.69(3H, s), 5.70(1H, s), 5.81(1H, s), 6.95–7.18(3H, m).
MS(ES, Pos); 455(M + 1)⁺

*³¹H NMR (200 MHz, CDCl₃); δ 1.02–1.38(12H, m), 2.03–2.43(2H, m), 2.21(3H, s), 2.37(3H, s), 2.72–3.08(3H, m), 3.17–4.35(6H, m), 4.15(2H, q, J=7.0Hz), 5.69(1H, s), 5.81(1H, s), 6.94–7.17(3H, m).
MS(ES, Pos); 469(M + 1)⁺

*⁴¹H NMR (200 MHz, CDCl₃); δ 0.03–0.48(4H, m), 1.04–1.39(10H, m), 2.08–2.34(2H, m), 2.19(3H,s), 2.33(3H,s), 2.80–3.07(3H, m), 3.15–3.74(5H, m), 4.02–4.33(1H, m), 4.15(2H, q, J=7.0Hz), 5.69(1H, s), 5.80(1H, s), 6.96–7.22(3H, m).
MS(SIMS, Pos); 495(M + 1)⁺

*⁵¹H NMR (200 MHz, CDCl₃); δ 1.20–1.35(9H, m), 2.10–2.33(2H, m), 2.19(3H, s), 2.36(3H, s), 2.78–3.06(3H, m), 3.30–3.74(4H, m), 3.90–4.30(1H, m), 4.15(2H, q, J=7.0Hz), 4.65–5.20(3H, m), 5.70(1H, s), 5.82(1H, s), 5.92–6.20(1H, m), 6.94–7.17(3H, m).
MS(SIMS, Pos); 481(M + 1)⁺

*⁶¹H NMR (200 MHz, CDCl₃); δ 1.19–1.36(9H, m), 2.08–2.38(3H, m), 2.22(3H, s), 2.38(3H, s), 2.80–3.05(3H, m), 3.35–3.77(4H, m), 4.00–4.30(1H, m), 4.16(2H, q, J=7.0Hz), 5.00–5.37(1H, m), 5.71(1H, s), 5.87(1H, s), 6.98–7.33(3H, m).
MS(SIMS, Pos); 479(M + 1)⁺

*⁷¹H NMR (200 MHz, CDCl₃); δ 1.13–1.38(12H, m), 1.87(3H, s), 2.18(3H, s), 2.26–2.77(4H, m), 2.36(3H, s), 2.95(1H, sept, J=7.0Hz), 3.33–4.32(6H, m), 4.19(2H, q, J=7.0Hz), 5.74(1H, s), 6.96–7.17(3H, m).
MS(ES, Pos); 483(M + 1)⁺

*⁸¹H NMR (200 MHz, CDCl₃); δ 1.21(3H, t, J=7.0Hz), 1.28(6H, d, J=7.0Hz), 2.04–2.41(2H, m), 2.21(3H, s), 2.36(3H, s), 2.80–3.06(3H, m), 3.23–4.39 (6H, m), 5.60(1H, s), 5.81(1H, s), 6.01(1H br, s), 6.93–7.15(3H, m).
MS(FAB, Pos); 441(M + 1)⁺

*⁹¹H NMR (200 MHz, CDCl₃); δ 1.21(3H, t, J=7.0Hz), 1.29(6H, d, J=7.0Hz), 2.10–2.35(2H, m), 2.23(3H, s), 2.37(3H, s), 2.41–2.59(2H, m), 2.94(1H, sept, J=7.0Hz), 3.31–4.38(6H, m), 5.14(1H, s), 5.83(1H, s), 6.98–7.18(3H, m).
MS(ES, Pos); 422(M + 1)⁺

*¹⁰¹H NMR (200 MHz, CDCl₃); δ 1.20(3H, t, J=7.0Hz), 1.27(6H, d, J=7.0Hz), 2.00–2.32(2H, m), 2.19(3H, s), 2.35(3H, s), 2.80–3.05(3H, m), 3.36–4.38 (6H, m), 5.36–5.71(3H, m), 5.73(1H, s), 6.96–7.18(3H, m).
MS(FAB, Pos); 440(M + 1)⁺

*¹¹¹H NMR (200 MHz, CDCl₃); δ 1.20(3H, t, J=7.0Hz), 1.27(6H, d, J=7.0Hz), 2.06–2.32(2H, m), 2.19(3H, s), 2.35(3H, s), 2.72–3.06(3H, m), 2.81(3H, d, J=5.0Hz), 3.23–4.35(6H, m), 5.35–5.60(1H, m), 5.55(1H, s), 5.80(1H, s), 6.92–7.16(3H, m).
MS(FAB, P06); 454(M + 1)⁺

*¹²¹H NMR (200 MHz, CDCl₃); δ 1.20(3H, t, J=7.0HZ), 1.26(6H, d, J=7.0HZ), 2.06–2.30(2H, m), 2.20(3H, s), 2.36(3H, s), 2.46–2.61(2H, m), 2.80–3.10 (1H, m), 2.97(3H, s), 3.01(3H, s), 3.31–4.39(6H, m), 5.80(1H,s), 6.94–7.17(3H, m).
MS(FAB, Pos); 468(M + 1)⁺

*¹³HCl salt, ¹H NMR (200 MHz, CDCl₃); δ 1.03–1.53(9H, m), 1.60–4.88(14H, m), 2.41(3H, s), 4.45(2H, d, J=5.0Hz), 5.56–6.62(3H, m), 6.84–7.59(8H, m), 13.37(1H, br s).
MS(FAB, Pos); 530(M + 1)⁺

*¹⁴¹H NMR (200 MHz, CDCl₃); δ 1.20(3H, t, J=7.0Hz), 1.28(6H, d, J=7.0Hz), 1.75–2.03(4H, m), 2.09–2.32(2H, x), 2.20(3H, s), 2.35(3H, s), 2.70–2.90 (2H, m), 2.95(1H, sept, J=7.0Hz), 3.33–4.33(10H, m), 5.81(1H,s), 5.83(1H, s), 6.96–7.15(3H, m).
MS(FAB, Pos); 494(M + 1)⁺

*¹⁵¹H NMR (200 MHz, CDCl₃); δ 1.20(3H, t, J=7.0Hz), 1.27(6H, d, J=7.0Hz), 2.10–2.30(2H, m), 2.20(3H, s), 2.36(3H, s), 2.41–2.60(2H, m), 2.96(1H, sept, J=7.0Hz), 3.27–4.40(14H, m), 5.81(1H, s), 6.95–7.16(3H, m).
MS(FAB, Pos); 510(M + 1)⁺

TABLE 17[*1]

Structure: imidazo-pyridine core with R5, Ar on N, A substituent, R4 substituent.

| Com. No. | Ex. No. | A | R4 | R5 | Ar | Melting point (° C.) (solvent for crystallization) |
|---|---|---|---|---|---|---|
| 17-01 | 1 | H2NCO-(tetrahydropyridinyl)- | CH3 | H | 2,4,6-trimethylphenyl | 209.0–211.0(AcOEt/IPE) |
| 17-02 | 1 | H2NCO-(tetrahydropyridinyl)- | CH3 | CH2CH3 | 2,4,6-trimethylphenyl | 202.0–204.0(AcOEt/IPE) |

[*1]Com. No. = compound number, Ex. No. = example number, solvent for crystallization; AcOEt = ethyl acetate, IPE = diisopropyl ether

TABLE 18[*1]

Structure: triazolo-pyridine core with Ar on N, A substituent, R4 substituent.

| Com. No. | Ex. No. | A | R4 | Ar | Melting point (° C.) (solvent for crystallization) |
|---|---|---|---|---|---|
| 18-01 | 1 | H2NCO-(tetrahydropyridinyl)- | CH3 | 2,4,6-trimethylphenyl | 230.0–231.0(EtOH) |

[*1]Com. No. = compound number, Ex. No. = example number, solvent for crystallization; EtOH = ethanol

TABLE 19*[1]

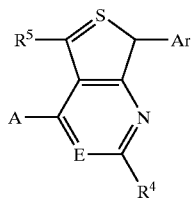

| Com. No. | Ex. No. | A | E | R[4] | R[5] | Ar | Melting point (° C.) (solvent for crystallization) |
|---|---|---|---|---|---|---|---|
| 19-01 | 2 | H₂NCO–⟨piperidinyl⟩– | N | CH₃ | H | 2,4-dichlorophenyl | 213.0–215.0(EtOH) |

*[1]Com. No. = compound number, Ex. No. = example number, solvent for crystallization; EtOH = ethanol

TABLE 20*[1]

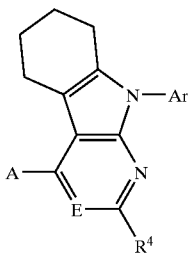

| Com. No. | Ex. No. | A | E | R[4] | Ar | Melting point (° C.) (solvent for crystallization) |
|---|---|---|---|---|---|---|
| 20-01 | 2 | H₂NCO–⟨piperidinyl⟩– | N | CH₃ | 2,4-dichlorophenyl | 247.0–249.0(AcOEt) |
| 20-02 | 2 | H₂NCO–⟨tetrahydropyridinyl⟩– | N | CH₃ | 2,4-dichlorophenyl | 181.0–183.0(AcOEt) |

*[1]Com. No. = compound number, Ex. No. = example number, solvent for crystallization; AcOEt = ethyl acetate Test Example [CRF Receptor Bonding Test]

Rat frontal cortex membranes or monkey amygdaloid body membranes were used as a receptor preparation.

$^{125}$I-CRF was used as $^{125}$I-labeled ligand.

Bonding reaction using the $^{125}$I-labeled ligand was carried out by the following method described in The Journal of Neuroscience, 7, 88 (1987).

Preparation of a Receptor Membranes:

Rat frontal cortex or monkey amygdaloid body was homogenized in 50 mM Tris-HCl buffer (pH 7.0) containing 10 mM MgCl$_2$ and 2 mM EDTA and centrifuged at 48,000× g, and the precipitate was washed once with Tris-HCl buffer. The washed precipitate was suspended in 50 mM Tris-HCl buffer (pH 7.0) containing 10 mM MgCl$_2$, 2 mM EDTA, 0.1% bovine serum albumin and 100 kallikrein units/ml aprotinin, to obtain a membrane preparation.

CRF Receptor Bonding Test:

The membrane preparation (0.3 mg protein/ml), $^{125}$I-CRF (0.2 nM) and a test drug were reacted at 25° C. for 2 hours. After completion of the reaction, the reaction mixture was filtered by suction through a glass filter (GF/C) treated with 0.3% polyethylene-imine, and the glass filter was washed three times with phosphate-buffered saline containing 0.01% Triton X-100. After the washing, the radioactivity of the filter paper was measured in a gamma counter.

The amount of $^{125}$I-CRF bonded when the reaction was carried out in the presence of 1 μM CRF was taken as the degree of nonspecific binding of $^{125}$I-CRF, and the difference between the total degree of $^{125}$I-CRF binding and the degree of nonspecific $^{125}$I-CRF binding was taken as the degree of specific $^{125}$I-CRF binding. An inhibition curve was obtained by reacting a definite concentration (0.2 nM) of $^{125}$I-CRF with various concentrations of each test drug under the conditions described above. A concentration of the test drug at which binding of $^{125}$I-CRF is inhibited by 50% (IC$_{50}$) was determined from the inhibition curve.

As a result, it was found that compounds 1-01, 1-02, 1-05, 1-06, 1-07, 1-09, 1-10, 1-12, 1-15, 1-16, 12-01 to 12-09, 16-05, 16-06 and 16-12 can be exemplified as typical compounds having an $IC_{50}$ value of 500 nM or less.

Industrial Applicability

According to the present invention, compounds having a high affinity for CRF receptors have been provided. These compounds are effective against diseases in which CRF is considered to be involved, such as depression, anxiety, Alzheimer's disease, Parkinson's disease, Huntington's chorea, eating disorder, hypertension, gastral diseases, drug dependence, epilepsy, cerebral infarction, cerebral ischemia, cerebral edema, cephalic external wound, inflammation, immunity-related diseases, alpecia, etc.

What is claimed is:

1. A tetrahydropyridino or piperidino heterocyclic derivative represented by the formula [I]:

A-Het [I]

wherein A is a group represented by the following formula [II] or [III]:

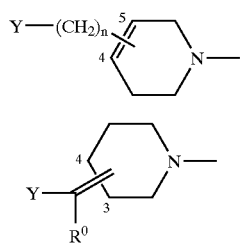

[II]

[III]

wherein the position of substitution by the $Y-(CH_2)_n-$ group of the group represented by the formula [II] is 4-position or 5-position, the position of substitution by the $Y-C(R^0)=$ group of the group represented by the formula [III] is 3-position or 4-position, $R^0$ is a hydrogen atom, a $C_{1-5}$alkyl group, a $C_{3-8}$cycloalkyl group or a $C_{3-8}$cycloalkyl-$C_{1-5}$alkyl group, n is an integer of 0 to 5, and Y is a cyano group, a group represented by the formula $-CONR^1(R^2)$ (wherein each of $R^1$ and $R^2$, which may be the same or different, is a hydrogen atom, a $C_{1-5}$alkyl group, a $C_{3-8}$cycloalkyl group, a $C_{3-8}$cycloalkyl-$C_{1-5}$alkyl group, a $C_{1-5}$alkoxy-$C_{1-5}$alkyl group, a $C_{3-8}$cycloalkyloxy-$C_{1-5}$alkyl group or a phenyl group, or $R^1$ and $R^2$, when taken together with the adjacent nitrogen atom, represent a 5- to 8-membered saturated heterocyclic group represented by the formula:

(wherein B is $CH_2$, NH, N—$C_{1-5}$alkyl, N—$C_{3-8}$cycloalkyl, N—$C_{1-5}$alkyl-$C_{3-8}$cycloalkyl, O or S)) or a group represented by the formula $-CO_2R^3$ (wherein $R^3$ is a hydrogen atom, a $C_{1-5}$alkyl group, a $C_{3-8}$cycloalkyl group, a $C_{3-8}$cycloalkyl-$C_{1-5}$alkyl group, a $C_{1-5}$alkoxy-$C_{1-5}$alkyl group, a $C_{3-8}$cycloalkyloxy-$C_{1-5}$alkyl group or a phenyl group), and Het is represented by the following formula:

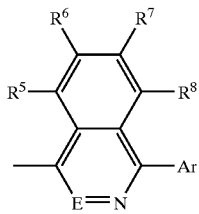

form (13)

wherein E is CH or N, each of $R^5$, $R^6$, $R^7$ and $R^8$, which may be the same or different, is a hydrogen atom, a halogen atom, a $C_{1-5}$alkyl group, a $C_{3-8}$cycloalkyl group, a $C_{3-8}$cycloalkyl-$C_{1-5}$alkyl group, a hydroxyl group, a $C_{1-5}$alkoxy group, a $C_{3-8}$cycloalkyloxy group, a group represented by the formula $-N(R^{12})R^{13}$ (wherein each of $R^{12}$ and $R^{13}$, which may be the same or different, is a hydrogen atom, a $C_{1-5}$alkyl group, a $C_{3-8}$cycloalkyl group or a $C_{3-8}$cycloalkyl-$C_{1-5}$alkyl group), a group represented by the formula $-CO_2R^{14}$ (wherein $R^{14}$ is a hydrogen atom, a $C_{1-5}$alkyl group, a $C_{3-8}$cycloalkyl group, a $C_{3-8}$cycloalkyl-$C_{1-5}$alkyl group, a $C_{1-5}$alkoxy-$C_{1-5}$alkyl group, a $C_{3-8}$alkyloxy-$C_{1-5}$alkyl group or a phenyl group), a cyano group, a nitro group, a $C_{1-5}$alkylthio group, a trifluoromethyl group or a trifluoromethoxy group, Ar is an aryl or heteroaryl group unsubstituted or substituted with 1 to 3 substituents which may be the same or different and are selected from halogen atoms, $C_{1-5}$alkyl groups, $C_{1-5}$alkoxy groups, $C_{1-5}$alkylthio groups, trifluoromethyl group, trifluoromethoxy group and groups represented by the formula $-N(R^{15})R^{16}$ (wherein each of $R^{15}$ and $R^{16}$, which may be the same or different, is a hydrogen atom or a $C_{1-5}$alkyl group), wherein said heteroaryl group is a heterocyclic soup having in its ring 1 to 4 heteroatoms, which may be the same or different and which are selected from the group consisting of nitrogen, oxygen and sulfur;

or a pharmaceutically acceptable salt thereof or its hydrate.

2. The tetrahydropyridino heterocyclic derivative, a pharmaceutically acceptable salt thereof or its hydrate according to claim 1, which is a compound represented by the formula [IV]:

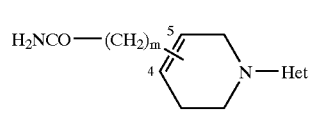

[IV]

wherein Het is form (13), and m is 0 or 1.

3. A pharmaceutical composition, comprising a tetrahydropyridino heterocyclic derivative, a pharmaceutically acceptable salt thereof or its hydrate according to any one of claims 1 or 2, as an active ingredient, and a pharmaceutically acceptable carrier.

4. A method of treating depression or anxiety, said method comprising administering to a subject an effective amount of a tetrahydropyridino heterocyclic derivative, a pharmaceutically acceptable salt thereof or its hydrate according to claims 1 or 2.

* * * * *